United States Patent
Wirth et al.

(10) Patent No.: US 10,308,632 B2
(45) Date of Patent: Jun. 4, 2019

(54) ANTIFUNGAL COMPOUNDS AND PROCESSES FOR MAKING

(71) Applicant: VPS-3, Inc., Durham, NC (US)

(72) Inventors: David Dale Wirth, Oak Ridge, NC (US); Christopher M. Yates, Raleigh, NC (US)

(73) Assignee: VPS-3, Inc., Durham, NC (US)

( * ) Notice: Subject to any disclaimer, the term of this patent is extended or adjusted under 35 U.S.C. 154(b) by 0 days.

(21) Appl. No.: 15/760,917

(22) PCT Filed: Sep. 16, 2016

(86) PCT No.: PCT/US2016/052300
§ 371 (c)(1),
(2) Date: Mar. 16, 2018

(87) PCT Pub. No.: WO2017/049196
PCT Pub. Date: Mar. 23, 2017

(65) Prior Publication Data
US 2018/0265492 A1  Sep. 20, 2018

Related U.S. Application Data

(60) Provisional application No. 62/275,504, filed on Jan. 6, 2016, provisional application No. 62/220,384, filed on Sep. 18, 2015.

(51) Int. Cl.
| *C07D 401/06* | (2006.01) |
| *C07D 453/02* | (2006.01) |
| *C07D 213/30* | (2006.01) |
| *C07C 303/44* | (2006.01) |
| *C07C 309/30* | (2006.01) |

(52) U.S. Cl.
CPC .......... *C07D 401/06* (2013.01); *C07C 303/44* (2013.01); *C07C 309/30* (2013.01); *C07D 213/30* (2013.01); *C07D 453/02* (2013.01); *C07B 2200/13* (2013.01)

(58) Field of Classification Search
CPC .................................................. C07D 401/06
USPC ........................................ 546/268.4; 514/340
See application file for complete search history.

(56) References Cited

U.S. PATENT DOCUMENTS

| 4,404,216 A | 9/1983 | Richardson et al. |
| 4,616,026 A | 10/1986 | Richardson et al. |
| 8,883,797 B2 | 11/2014 | Hoekstra et al. |
| 9,309,273 B2 | 4/2016 | Hoekstra et al. |
| 2005/0209259 A1 | 9/2005 | Huang |
| 2009/0306066 A1 | 12/2009 | Qin et al. |
| 2012/0329802 A1 | 12/2012 | Hoekstra et al. |
| 2013/0005719 A1 | 1/2013 | Hoekstra et al. |
| 2013/0338172 A1 | 12/2013 | Smyth et al. |
| 2014/0349973 A1 | 11/2014 | Hoekstra et al. |
| 2015/0051199 A1 | 2/2015 | Woodhead et al. |

FOREIGN PATENT DOCUMENTS

| CN | 103857675 A | 6/2014 |
| CN | 103930418 A | 7/2014 |
| EP | 0 069 442 A1 | 1/1983 |
| JP | 58-032868 A | 2/1983 |
| WO | WO 2004/108684 A1 | 12/2004 |
| WO | WO 2011/133875 A2 | 10/2011 |
| WO | WO 2013/090210 A1 | 6/2013 |
| WO | WO 2014/201161 A1 | 12/2014 |
| WO | WO 2015/143142 A1 | 9/2015 |
| WO | WO 2016/149486 A1 | 9/2016 |

OTHER PUBLICATIONS

Chinese Office Action for Application No. 201280069217.7 dated Apr. 29, 2015.
Eurasian Office Action for Application No. 201491151/28 dated Mar. 12, 2015.
Extended European Search Report for Application No. 12858190.7 dated May 8, 2015.
Extended European Search Report for Application No. 18158614.0 dated May 4, 2018.
International Search Report and Written Opinion for Application No. PCT/US2012/068818 dated Mar. 19, 2013.
International Search Report and Written Opinion dated Nov. 18, 2016 in connection with Application No. PCT/US2016/052151.
International Search Report and Written Opinion dated Feb. 2, 2017 in connection with Application No. PCT/US2016/052300.
Invitation to Pay Additional Fees dated Nov. 10, 2016 in connection with Application No. PCT/US2016/052300.
Böhme et al., Treatment of invasive fungal infections in cancer patients—recommendations of the Infectious Diseases Working Party (AGIHO) of the German Society of Hematology and Oncology (DGHO). Ann Hematol. Feb. 2009;88(2):97-110. doi: 10.1007/s00277-008-0622-5. Epub Oct. 14, 2008. Review.
Chen et al., Structural basis for multifunctional roles of mammalian aminopeptidase N. Proc Natl Acad Sci U S A. Oct. 30, 2012;109(44):17966-71. doi: 10.1073/pnas.1210123109. Epub Oct. 15, 2012.
Cornelison, Human papillomavirus genotype 16 vaccines for cervical cancer prophylaxis and treatment. Curr Opin Oncol. Sep. 2000;12(5):466-73. Review.
Curtis et al., Naturally occurring thiophens. V. Acetylenic thiophens from the basidiomycete Daedalea juniperina Murr. J Chem Soc Perkin 1. 1969;13:1813-8.
Eto et al., New antifungal 1,2,4-triazoles with difluoro(heteroaryl)methyl moiety. Chem Pharm Bull (Tokyo). Jul. 2000;48(7):982-90.
Swenson, New insights into carbonic anhydrase inhibition, vasodilation, and treatment of hypertensive-related diseases. Curr Hypertens Rep. Sep. 2014;16(9):467. doi: 10.1007/s11906-014-0467-3. Review.

*Primary Examiner* — Patricia L Morris

(57) ABSTRACT

Provided are polymorphic forms of compound 5 or 5*, or mixtures thereof, and polymorph forms of compound 14 or 14*, or mixtures thereof. Also provided are methods of preparing compound 5 or 5*, or mixtures thereof, and methods of preparing compound of 14 or 14*, or mixtures thereof, which are useful as antifungal agents. In particular, provided is new methodology for preparing polymorphs of the compounds described and substituted derivatives thereof.

3 Claims, 11 Drawing Sheets

| Angle 2-Theta ° | Intensity % | Angle 2-Theta ° | Intensity % |
|---|---|---|---|
| 4.8 | 100.0 | 18.5 | 37.1 |
| 8.8 | 25.7 | 19.1 | 6.9 |
| 9.2 | 10.5 | 19.6 | 12.6 |
| 9.6 | 8.5 | 20.6 | 7.1 |
| 10.3 | 6.0 | 21.5 | 8.2 |
| 10.6 | 18.5 | 23.3 | 7.5 |
| 12.9 | 6.6 | 23.7 | 46.4 |
| 14.1 | 11.6 | 25.1 | 9.9 |
| 14.4 | 9.7 | 26.0 | 5.4 |
| 14.9 | 2.4 | 26.5 | 5.9 |
| 15.1 | 2.6 | 27.9 | 6.1 |
| 16.0 | 4.9 | 28.3 | 5.6 |
| 16.6 | 9.1 | 29.0 | 6.0 |
| 17.6 | 6.5 | 30.0 | 6.4 |
| 18.1 | 7.3 | | |

FIG. 6 (Continued)

| Angle 2-Theta ° | Intensity % |
|---|---|
| 5.9 | 15 |
| 7.5 | 34 |
| 8.2 | 49 |
| 10.8 | 28 |
| 12.7 | 30 |
| 13.4 | 25 |
| 14.1 | 21 |
| 15.1 | 51 |
| 15.8 | 41 |
| 16 | 22 |
| 16.3 | 32 |
| 16.6 | 22 |
| 17.0 | 25 |
| 18.0 | 19 |
| 18.5 | 19 |
| 19 | 100 |
| 19.5 | 23 |
| 20.2 | 86 |
| 20.7 | 28 |
| 21.3 | 19 |
| 21.8 | 20 |
| 22.5 | 29 |
| 23.3 | 41 |
| 23.6 | 42 |
| 24.4 | 44 |
| 24.9 | 27 |
| 26.4 | 27 |
| 26.9 | 23 |
| 28.2 | 19 |
| 28.7 | 21 |

ANTIFUNGAL COMPOUNDS AND PROCESSES FOR MAKING

CROSS-REFERENCE TO RELATED APPLICATIONS

This application is the national Phase under 35 U.S.C. § 371 of PCT International Application No. PCT/US2016/052300, filed Sep. 16, 2016, which claims priority to U.S. Provisional Application No. 62/220,384, filed Sep. 18, 2015 and U.S. Provisional Application No. 62/275,504, filed Jan. 6, 2016, each of which is incorporated herein by reference in its entirety.

BACKGROUND

It is well known that the crystalline polymorph form of a particular drug is often an important determinant of the drug's ease of preparation, stability, solubility, storage stability, ease of formulation and in vivo pharmacology. Polymorphic forms occur where the same composition of matter crystallizes in a different lattice arrangement resulting in different thermodynamic properties and stabilities specific to the particular polymorph form. In cases where two or more polymorph substances can be produced, it is desirable to have a method to prepare each of the polymorphs in pure form. In deciding which polymorph is preferable, the numerous properties of the polymorphs must be compared and the preferred polymorph chosen based on the many physical property variables. It is entirely possible for example that one polymorph form can be preferable in some circumstances where certain aspects such as ease of preparation, stability, etc. are deemed to be especially important. In other situations, for example, a different polymorph may be preferred for greater solubility and/or superior pharmacokinetics.

Because improved drug formulations, showing, for example, better bioavailability or better stability are consistently sought, there is an ongoing need for new or purer polymorphic forms of existing drug molecules. The various crystalline polymorphs of Compounds 5 or 5* and 14 or 14* described herein help meet these and other needs.

BRIEF SUMMARY OF THE INVENTION

The invention is directed toward polymorph forms of compounds 5 or 5*, or mixtures thereof, and polymorph forms of compounds 14 or 14*, or mixtures thereof. The invention is also directed toward methods of synthesis of 5 or 5*, and methods of synthesis of 14 or 14*. The methods can comprise the compounds herein.

One aspect of the invention relates to polymorph forms of compounds of formula 5 or 5*, or a pharmaceutically acceptable salt, hydrate, solvate, complex or prodrug thereof.

5

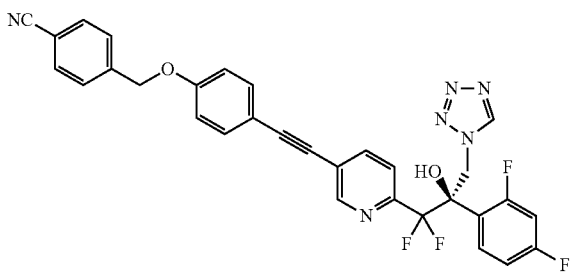

5*

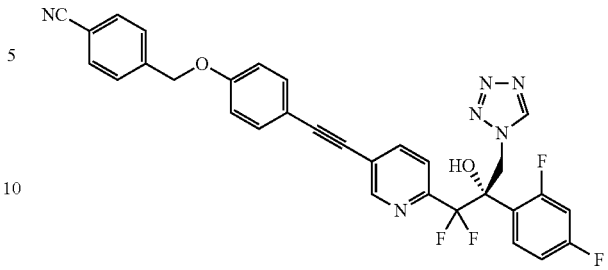

Another aspect of the invention relates to polymorph forms of compounds of formula 14 or 14*, or a pharmaceutically acceptable hydrate, solvate, complex or prodrug thereof.

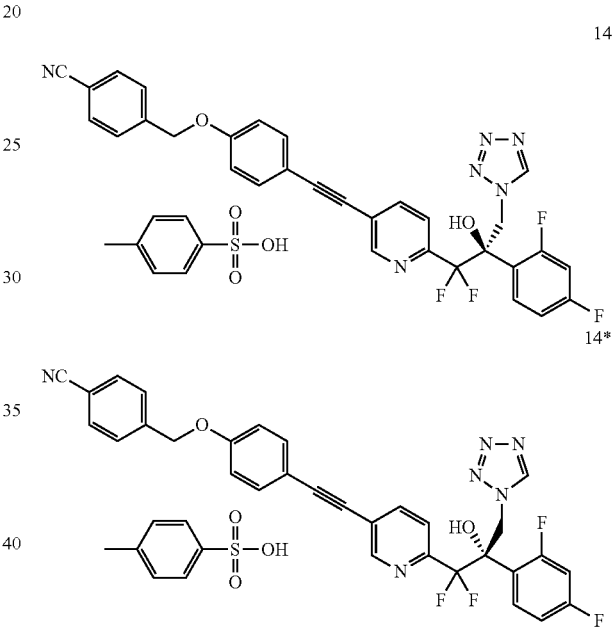

In another aspect, the invention is an anhydrous polymorphic form of a compound of any of the formulae herein. In other aspects, the anhydrous form of a compound of any of the formulae herein is isolated. In other aspects, the anhydrous form of a compound of any of the formulae herein is isolated and has less than 2 weight % water therein (e.g., <1 wt. %, <0.5 wt. %, <0.25 wt. %, <0.1 wt. %). In other aspects, the anhydrous form of a compound of any of the formulae herein is isolated and has less than 750 ppm water therein (e.g., <500 ppm, <400 ppm, <300 ppm, <250 ppm, <200 ppm, <150 ppm, <100 ppm, <50 ppm, <20 ppm, <10 ppm, <1 ppm). In other aspects, the anhydrous form is essentially free of water. In other aspects, the anhydrous form is substantially free of water.

In another aspect, the invention is a salt, hydrate, or solvate form of a compound of any of the formulae herein, having the physicochemical characteristics described herein.

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In the following aspects, reference is made to the schemes and compounds herein, including the reagents and reaction conditions delineated herein. Other aspects include any of the compounds, reagents, transformations or methods thereof delineated in the examples herein (in whole or in part), including as embodiments with single elements (e.g., compounds or transformations) or embodiments including multiple elements (e.g., compounds or transformations). Other aspects include any of the compounds of the formulae herein as characterized by the physicochemical characteristics described in the examples, figures, tables or any portion of the specification herein.

In another aspect, the invention provides a method to prepare an anhydrous form of any compound of a formulae herein comprising placing a compound of a formulae herein in a solvent and recrystallizing and isolating the compound as an anhydrous form of the compound. In certain embodiments, the method further comprises: heating at a temperature of about 25° C. or higher (e.g., 30° C. or higher; 35° C. or higher; 40° C. or higher; 45° C. or higher; 50° C. or higher; 55° C. or higher; 60° C. or higher; 65° C. or higher; 70° C. or higher; 75° C. or higher; 80° C. or higher; 85° C. or higher; 90° C. or higher; 95° C. or higher; or 100° C. or higher). In another aspect, the method further comprises: drying the resulting anhydrous compound; drying the resulting anhydrous compound under vacuum; drying the resulting anhydrous compound under vacuum at about 25° C. or higher (e.g., 30° C. or higher; 35° C. or higher; 40° C. or higher; 45° C. or higher; 50° C. or higher; 55° C. or higher; 60° C. or higher; 65° C. or higher; 70° C. or higher; 75° C. or higher; 80° C. or higher; 85° C. or higher; 90° C. or higher; 95° C. or higher; or 100° C. or higher).

In aspects, the method above comprises at least one solvent. In certain embodiments, the solvent is an organic solvent (e.g., hydrocarbons, ethers, ketones, esters, alcohols, amides, acetonitrile, and the like); two or more solvents (e.g., a combination of two different organic solvents); or three or more solvents (e.g., a combination of three different organic solvents). Solvents useful herein are known in the art.

In aspects, the method above comprises: an organic solvent comprising at least one oxygen (e.g., alcohols, ethers, ketones, esters, amides, and the like), or a hydrocarbon solvent (e.g., n-pentane, n-heptane, n-hexane, cyclohexane, methylcyclohexane, and the like); two or more solvents (e.g., a combination of an organic solvent and a different organic solvent, wherein the different organic solvent comprises at least one oxygen; a combination of a ketone and a hydrocarbon; acetone and n-heptane); or three or more solvents. In another aspect, the method comprises a combination of solvents, wherein said combination contains <15% (w/w) total amount of water, methanol, and ethanol. In another aspect, the combination of solvents is acetone and n-heptane. In another aspect, the solvent is i-propanol. In another aspect, the solvent is isopropyl acetate. In another aspect, the solvent is toluene. Solvents useful herein are known in the art.

In another aspect, the invention is an anhydrous form of a compound of any of the formulae herein, made by a process described herein.

Another aspect of the invention relates to a process for preparing a polymorph form of a compound of formula 5 or 5*, or a pharmaceutically acceptable salt, hydrate, solvate, complex or prodrug thereof.

Another aspect of the invention relates to a process for preparing a polymorph form of a compound of formula 14 or 14*, or a pharmaceutically acceptable hydrate, solvate, complex or prodrug thereof.

In another aspect, the crystallization solvent or crystallization solvent mixture from any of the embodiments presented herein is ethyl acetate, isopropyl acetate, ethanol, methanol, acetone, i-propanol, toluene, n-heptane, or acetonitrile, or combinations thereof.

In another aspect, the crystallization co-solvent or crystallization co-solvent mixture from any of the embodiments presented herein is pentane, methyl t-butylether, hexane, n-heptane, or toluene, or combinations thereof.

In another aspect, any of the embodiments presented herein may comprise repeating the enantio-enrichment step(s) until desired level of enantio-enrichment is attained.

In another aspect, any of the embodiments presented herein may comprise repeating the enantio-enrichment step(s) and/or purification steps until desired level of enantio-enrichment and/or purification is attained.

In other aspects, the invention provides a compound of any of the formulae herein, wherein the compound inhibits (or is identified to inhibit) lanosterol demethylase (CYP51).

In another aspect, the invention provides a pharmaceutical composition comprising a compound of any formulae herein and a pharmaceutically acceptable carrier.

In other aspects, the invention provides a method of modulating metalloenzyme activity in a subject, comprising contacting the subject with a compound of any formulae herein, in an amount and under conditions sufficient to modulate metalloenzyme activity.

In one aspect, the invention provides a method of treating a subject suffering from or susceptible to a metalloenzyme-related disorder or disease, comprising administering to the subject an effective amount of a compound or pharmaceutical composition of any formulae herein.

In another aspect, the invention provides a method of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of any formulae herein, such that said subject is treated for said disorder.

In another aspect, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any formulae herein, such that metalloenzyme activity in said subject is modulated (e.g., down regulated, inhibited). In another aspect, the compounds delineated herein preferentially target cancer cells over nontransformed cells.

DETAILED DESCRIPTION

Definitions

Figure 1:
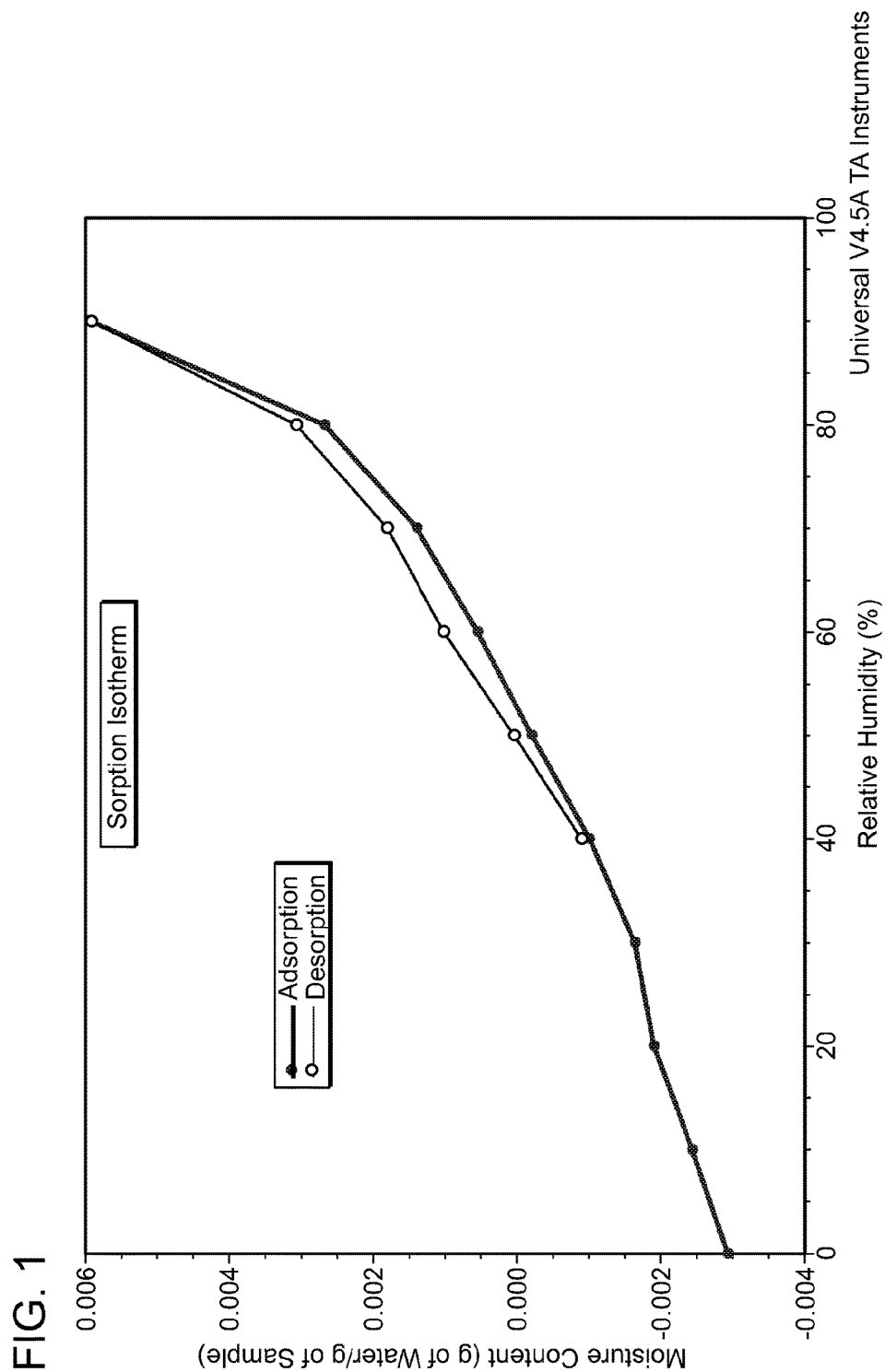
FIG. 1: depicts a DVS analysis of an anhydrous form of compound 14 (Form 1).

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore, the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The sp² or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "haloalkoxy" refers to an —O-alkyl radical that is substituted by one or more halo substituents. Examples of haloalkoxy groups include trifluoromethoxy, and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF₃), sulfonates (e.g., mesyl, tosyl), acetamides (e.g., —NHC(O)Me), carbamates (e.g., N(Me)C(O)Ot-Bu), phosphonates (e.g., —OP(O)(OEt)₂), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; aryl alkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N''-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g., *Design And Optimization in Organic Synthesis, 2ⁿᵈ Edition*, Carlson R, Ed, 2005; Elsevier Science Ltd.; Jäh- nisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database. The invention includes the intermediate compounds used in making the compounds of the formulae herein as well as methods of making such compounds and intermediates, including without limitation those as specifically described in the examples herein.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Pharmaceutical Compositions

In one aspect, the invention provides a pharmaceutical composition comprising a compound of any formulae herein and a pharmaceutically acceptable carrier.

In another embodiment, the invention provides a pharmaceutical composition further comprising an additional therapeutic agent. In a further embodiment, the additional therapeutic agent is an anti-cancer agent, antifungal agent, cardiovascular agent, antiinflammatory agent, chemotherapeutic agent, an anti-angiogenesis agent, cytotoxic agent, an anti-proliferation agent, metabolic disease agent, opthalmologic disease agent, central nervous system (CNS) disease agent, urologic disease agent, or gastrointestinal disease agent.

In one aspect, the invention provides a kit comprising an effective amount of a compound of any formulae herein, in unit dosage form, together with instructions for administering the compound to a subject suffering from or susceptible to a metalloenzyme-mediated disease or disorder, including cancer, solid tumor, cardiovascular disease, inflammatory disease, infectious disease. In other embodiments the disease, disorder or symptom thereof is metabolic disease, opthalmologic disease, central nervous system (CNS) disease, urologic disease, or gastrointestinal disease.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/mL); benzalkonium chloride (0.1-0.2 mg/mL); polysorbate 80 (TWEEN® 80; 0.5-5 mg/mL); carboxymethylcellulose sodium or microcrystalline cellulose (1-15 mg/mL); phenylethanol (1-4 mg/mL); and dextrose (20-50 mg/mL). The pH of the final suspension can be adjusted to range from about pH5 to pH7, with a pH of about pH 5.5 being typical.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease. Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

Agricultural Applications

The compounds and compositions herein can be used in methods of modulating metalloenzyme activity in a microorganism on a plant comprising contacting a compound (or composition) herein with the plant (e.g., seed, seedling, grass, weed, grain). The compounds and compositions herein can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence. The administration can be either as a treatment or preventative regimen.

EXAMPLES

The present invention will now be demonstrated using specific examples that are not to be construed as limiting.

General Experimental Procedures

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate). The beam divergence, i.e. the effective size of the X-ray beam on the sample, was approximately 4 mm. A Θ-Θ continuous scan mode was employed with a sample—detector distance of 20 cm which gives an effective 2θ range of 3.2°-29.7°. Typically the sample would be exposed to the X-ray beam for 120 seconds. The software used for data collection was GADDS for XP/2000 4.1.43 and the data were analysed and presented using Diffrac Plus EVA v13.0.0.2 or v15.0.0.0. Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat-conducting compound. The sample was then heated to the appropriate temperature at 30° C./min and subsequently held isothermally for 1 minute before data collection was initiated.

X-Ray Powder Diffraction patterns were also collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0. Samples were run under ambient conditions as flat plate specimens using powder as received. The sample was gently packed into a cavity cut into polished, zero-background (510) silicon wafer. The sample was rotated in its own plane during analysis. The details of the data collection are: Angular range: 2 to 42° 2θ; Step size: 0.05° 2θ; Collection time: 0.5 s/step.

DSC data were collected on a TA Instruments Q2000 equipped with a 50 position autosampler. The calibration for thermal capacity was carried out using sapphire and the calibration for energy and temperature was carried out using certified indium. Typically, 1-3 mg of each sample, in a pin-holed aluminium pan, was heated at 10° C./min from 25° C. to 220° C. A purge of dry nitrogen at 50 mL/min was maintained over the sample. Modulated temperature DSC was carried out using an underlying heating rate of 2° C./min and temperature modulation parameters of ±0.636° C. (amplitude) every 60 seconds (period). The instrument control software was Advantage for Q Series v2.8.0.394 and Thermal Advantage v5.5.3 and the data were analysed using Universal Analysis v4.5A.

DSC data was also collected on a TA Instruments Discovery DSC equipped with a 50 position auto-sampler. The calibration for thermal capacity was carried out using sapphire and the calibration for energy and temperature was carried out using certified indium. Typically, 0.5-3 mg of each sample, in a pin-holed aluminium pan, was heated at 10° C./min from 25° C. up to 300° C. A purge of dry nitrogen at 50 mL/min was maintained over the sample. The instrument control and data analysis software was TRIOS v3.2.0.3877.

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in DMSO-$d_6$, unless otherwise stated. Off-line analysis was carried out using ACD Spectrus Processor 2012.

Fourier Transform—Infrared (FTIR) Data were collected on a Perkin-Elmer Spectrum One fitted with a universal Attenuated Total Reflectance (ATR) sampling accessory. The data were collected and analysed using Spectrum v10.0.1 software.

Thermo-gravimetric analysis (TGA) data were collected on a TA Instruments Discovery TGA, equipped with a 25 position auto-sampler. The instrument was temperature calibrated using certified alumel and nickel. Typically, 3-10 mg of each sample was loaded onto a pre-tared aluminium pan and heated at 10° C./min from ambient temperature to 350° C. A nitrogen purge at 25 mL/min was maintained over the sample. The instrument control and data analysis software was TRIOS v3.2.0.3877.

Scanning electron microscopy (SEM) data were collected on a Phenom Pro Scanning Electron Microscope. A small quantity of sample was mounted onto an aluminium stub using conducting double-sided adhesive tape. A thin layer of gold was applied using a sputter coater (20 mA, 120 s).

Purity analysis was performed on an Agilent HP1100 series HPLC system equipped with a diode array detector and using ChemStation software vB.04.03 using the method detailed below:

| Parameter | Value |
|---|---|
| Sample Preparation | 0.3-0.5 mg/ml in acetonitrile:water 1:1 |
| Column | Supelco Ascentis Express C18, 100 × 4.6 mm, 2.7 μm |
| Column Temperature (° C.) | 25 |
| Injection (μL) | 5 |
| Wavelength, Bandwidth (nm) | 255, 90 |
| Flow Rate (ml/min) | 2 |
| Phase A | 0.1% TFA in water |
| Phase B | 0.085% TFA in acetonitrile |

| | Time (min) | % Phase A | % Phase B |
|---|---|---|---|
| Timetable | 0 | 95 | 5 |
| | 6 | 5 | 95 |
| | 6.2 | 95 | 5 |
| | 8 | 95 | 5 |

Gravimetric Vapor Sorption (GVS) isotherms were obtained using a SMS DVS Intrinsic moisture sorption analyser, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 mL/min The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). Typically. 10-15 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was undertaken in Microsoft Excel using DVS Analysis Suite v6.2 (or 6.1 or 6.0).

Method Parameters for SMS DVS Intrinsic Experiments

| Parameters | Values |
|---|---|
| Adsorption-Scan 1 | 40-90 |
| Desorption/Adsorption-Scan 2 | 90-0, 0-40 |
| Intervals (% RH) | 10 |
| Number of Scans | 4 |
| Flow rate (mL/min) | 200 |
| Temperature (° C.) | 25 |
| Stability (° C./min) | 0.2 |
| Sorption Time (hours) | 6 hour time out |

The sample was recovered after completion of the isotherm and re-analysed by XRPD.

Definitions of variables in the structures in schemes herein are commensurate with those of corresponding positions in the formulae delineated herein.

Synthesis of 5 or 5*

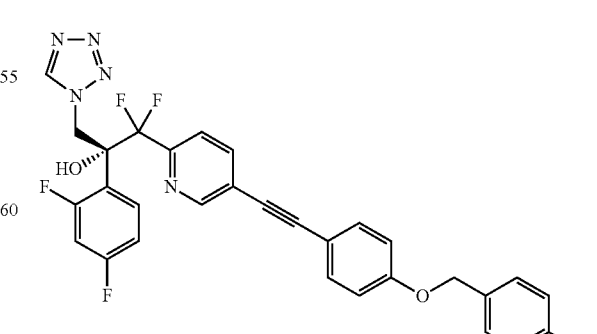

5

-continued

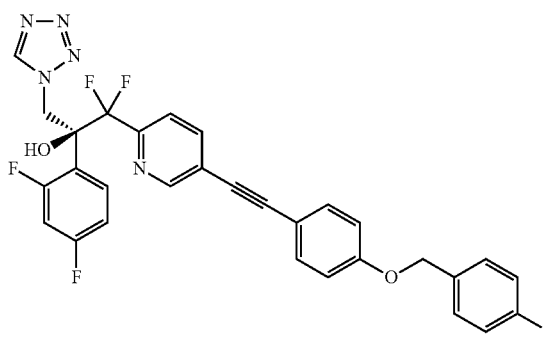

5*

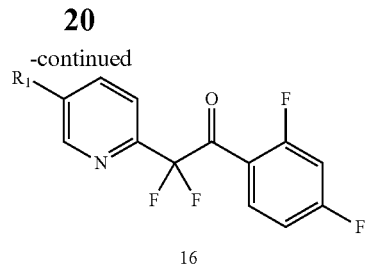

16

$R_1$ = halo, —O(C=O)-alkyl, —O(C=O)-substituted alkyl,
—O(C=O)-aryl, —O(C=O)-substituted aryl, —O(C=O)—O-alkyl,-
O(C=O)—O-substituted alkyl, —O(C=O)—O-aryl,
—O(C=O)—O-substituted aryl, —O(SO$_2$)-alkyl,
—O(SO$_2$)-substituted alkyl,- O(SO$_2$)-aryl, or —O(SO$_2$)-substituted aryl.

A process to prepare enantiopure compound 5 or 5* is disclosed. Syntheses of 5 or 5* may be accomplished using the example syntheses that are shown below (Schemes 1-4). The preparation of precursor ketone 16-Br is performed starting with reaction of 2,5-dibromo-pyridine with ethyl 2-bromo-difluoroacetate to produce ester 15-Br. This ester can be reacted with morpholine to furnish morpholine amide 15b-Br, followed by arylation to provide ketone 16-Br. Alternatively, ketone 16-Br can be afforded directly from ester 15-Br, as shown in Scheme 1.

Ketone 16 may be used to prepare 13 (or 13*, the enantiomer of 13, or mixtures thereof) or 5 (or 5*, the enantiomer of 5, or mixtures thereof) by the following three-step process (Scheme 3). In the presence of a chiral Scheme 1. Synthesis of ketone 16-Br

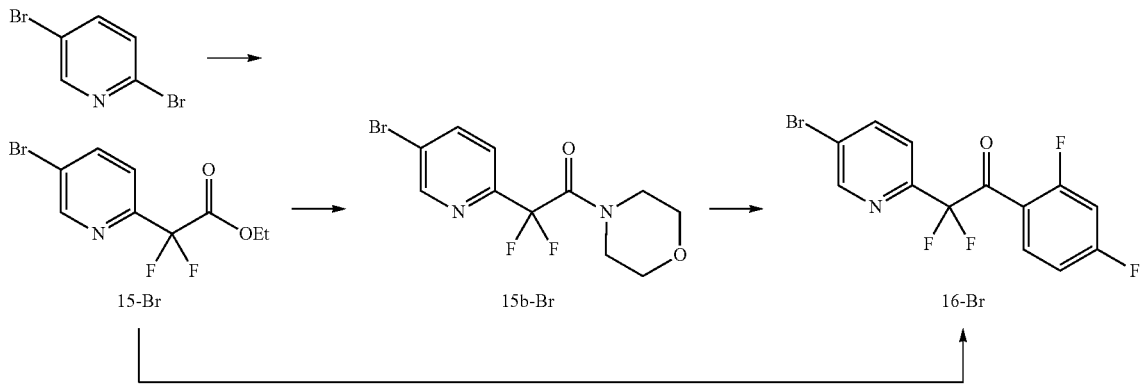

Ketone 16 may be prepared in an analogous fashion as described in Scheme 1 starting from corresponding substituted 2-bromo-pyridines, which can be prepared according to synthetic transformations known in the art and contained in the references cited herein (Scheme 2).

Scheme 2. Synthesis of ketone 16

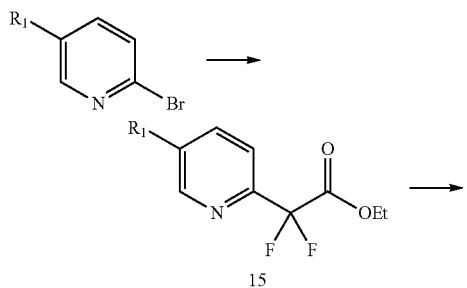

catalyst/reagent (e.g. compounds of Formula 3 or 3*), base-treated nitromethane is added to 16 or 16-1 to furnish 7 (or 7*, the enantiomer of 7, or mixtures thereof) or 7-1 (or 7*-1, the enantiomer of 7-1, or mixtures thereof), respectively. Reduction of 7 (or 7*, the enantiomer of 7, or mixtures thereof) or 7-1 (or 7*-1, the enantiomer of 7-1, or mixtures thereof) (e.g. hydrogenation) produces 11 (or 11*, the enantiomer of 11, or mixtures thereof) or 4 (or 4*, the enantiomer of 4, or mixtures thereof). Annulation of 11 (or 11*, the enantiomer of 11, or mixtures thereof) or 4 (or 4*, the enantiomer of 4, or mixtures thereof) by treatment with sodium azide/trimethylorthoformate furnishes tetrazoles 13 (or 13*, the enantiomer of 13, or mixtures thereof) or 5 (or 5*, the enantiomer of 5, or mixtures thereof). Sonogashira coupling of 13 or 13* (e.g., 13 or 13*, wherein R=Br; also referred to as 13-Br or 13*-Br) with 4-((4-ethynylphenoxy)methyl)benzonitrile produces 5 (or 5*, the enantiomer of 5, or mixtures thereof).

Scheme 3. Asymmetric Henry reaction

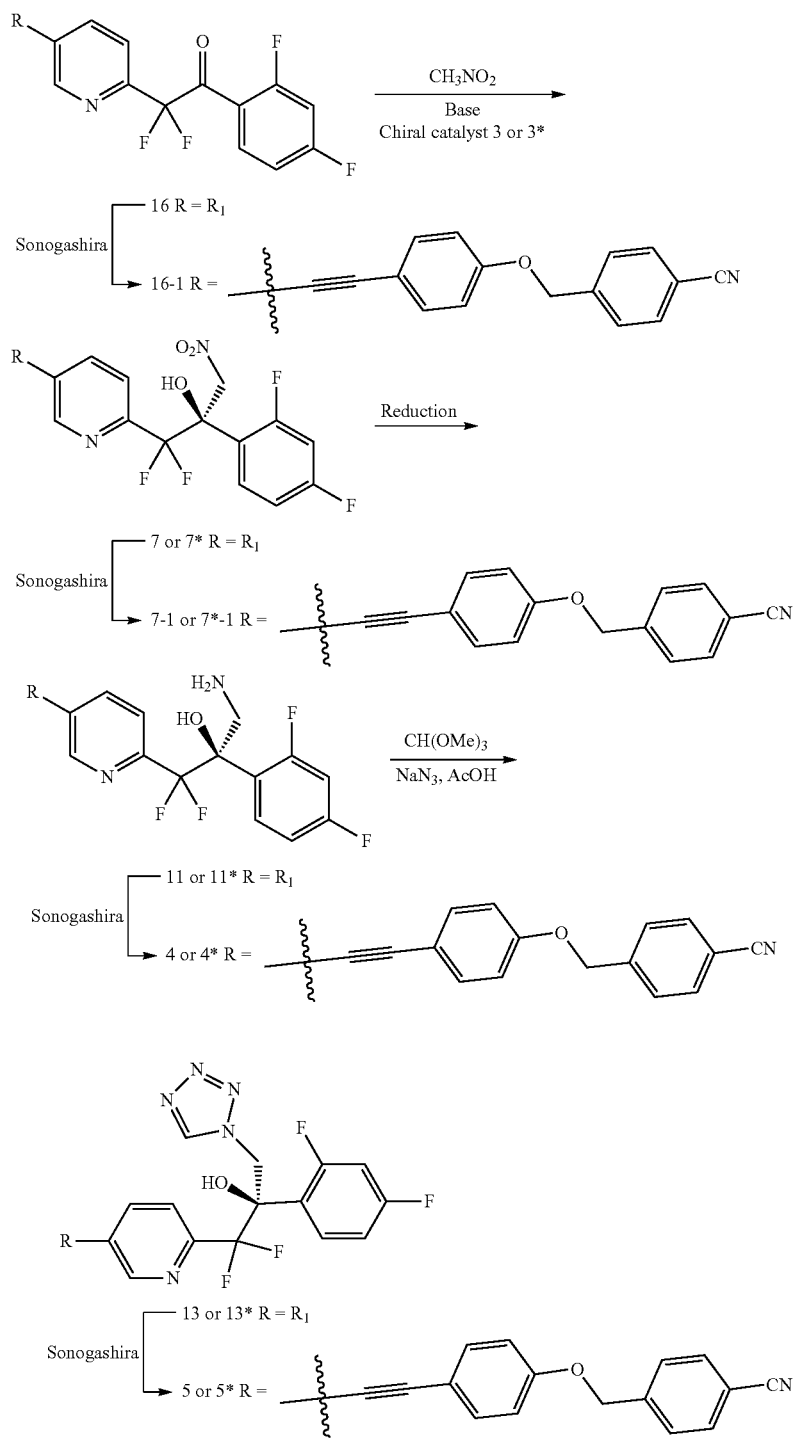

$R_1$ = halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

Compound 5 (or 5*, the enantiomer of 5, or mixtures thereof) prepared by any of the methods presented herein can be converted to a sulfonic acid salt of formula 14 (or 14*, the enantiomer of 14, or mixtures thereof), as shown in Scheme 4. This can be accomplished by a) combining compound 5 (or 5*, the enantiomer of 5, or mixtures thereof), a crystallization solvent or crystallization solvent mixture (e.g., EtOAc, iPrOAc, EtOH, MeOH, or acetonitrile, or combinations thereof), and a sulfonic acid

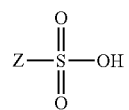 5
(e.g., Z=Ph, p-tolyl, Me, or Et), and b) filtering the mixture to obtain a sulfonic acid salt of formula 14 (or 14*, the enantiomer of 14, or mixtures thereof).

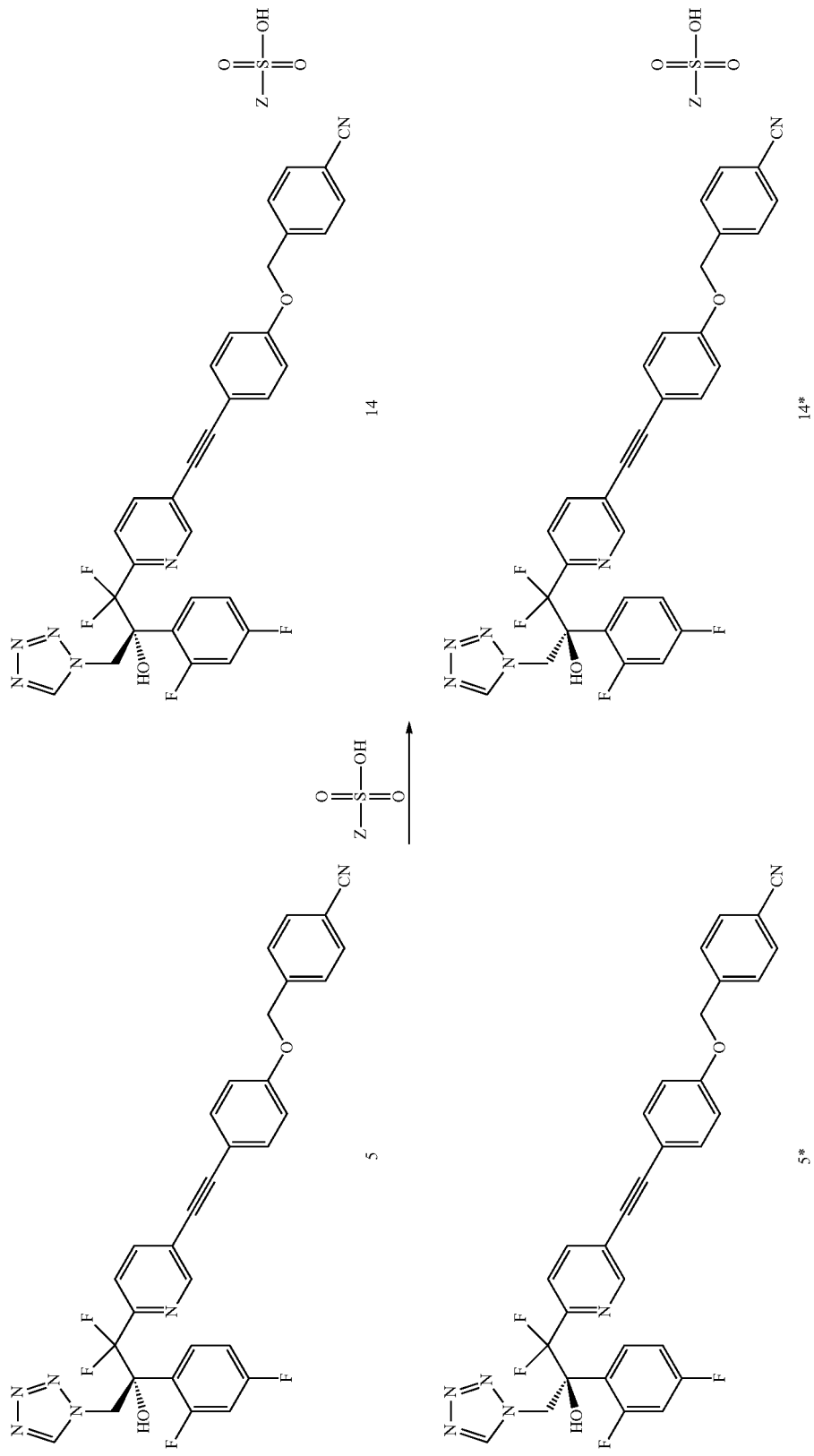

| Abbreviations: | |
|---|---|
| A % | area percent |
| AcOH | acetic acid |
| ACN | acetonitrile |
| Amt | amount |
| API | active pharmaceutical ingredient |
| Aq. | aqueous |
| Besylate, Bs | benzenesulfonic acid |
| DEA | diethylamine |
| DMF | N,N-dimethylformamide |
| DMSO | dimethylsulfoxide |
| Eq, equiv | equivalent |
| $Et_3N$ | triethylamine |
| EtOH | ethanol |
| FID | Flame ionization detector |
| GC | gas chromatography |
| HPLC | high performance liquid chromatography |
| ID | identification |
| IPA | isopropanol |
| IPrMgCl | isopropylmagnesium chloride |
| K-OtBu | potassium tert-butoxide |
| L-DTTA | di-O-p-toluoyl-L-tartaric acid |
| M | mole/liter |
| MeOH | methanol |
| Min | minutes |
| Mol | moles |
| MTBE | tert-butyl methyl ether |
| MW | molecular weight |
| NA | not applicable |
| $Na_2EDTA \cdot 2H_2O$ | ethylenediaminetetraacetic acid disodium salt dihydrate |
| ND | not detected |
| NMR | nuclear magnetic resonance spectroscopy |
| ppm | parts per million |
| THF | tetrahydrofuran |
| TLC | thin layer chromatography |
| TMS | trimethylsilyl |
| TMSI | trimethylsulfoxonium iodide |
| Tosylate, Ts | p-Toluenesulfonate |
| Wt | weight |
| XRD | x-ray powder diffraction |

The following analytical techniques were employed:
In-Process GC Analyses:
Column: DB-624, 30 m×0.25 mm, 1.4 μm
Carrier gas: Hydrogen
Flow rate: 20 psi
Inlet Pressure: 20 psi
Split ratio: 50:1
Injection temperature: 250° C.
Inj volume: 1 μL
Oven program: 60° C. (3 min hold), 40° C./min to 240° C., 23 min hold at 240° C.
Detector: FID, 280° C.
In-Process HPLC Analyses:
Column: XBridge BEH C18, 2.1×50 mm, 2.5 μm
Mobile Phase: A=0.1% $TFA/H_2O$, B=0.1% TFA/ACN
Autosampler flush: 1:1 $ACN/H_2O$
Flow Rate: 0.8 ml/min
Temperature: 50° C.
Detector: UV 218 nm
Pump Parameters:

| Step | Segment Time | A | B | Curve |
|---|---|---|---|---|
| 0 | 0.5 | 90.0 | 10.0 | 0 |
| 1 | 0.5 | 90.0 | 10.0 | 0 |
| 2 | 6.0 | 10.0 | 90.0 | 1 |
| 3 | 1.1 | 10.0 | 90.0 | 0 |
| 4 | 4.0 | 90.0 | 10.0 | 0 |

HPLC Method Used in Assessing HPLC Purity of 5 and 5*; and 14 and 14*:
Column: Waters Sunfire C18, 3.5 μm, 4.6×150 mm
Mobile Phase: A=0.05% $H_3PO_4$ in water, B=0.05% $H_3PO_4$ in ACN; C=NA; D=0.05% $H_3PO_4$ in methanol
Diluent: ACN
Autosampler flush: 1:1 ACN/H2O
Flow Rate: 1.0 ml/min
Temperature: 30° C.
Detector: UV 225 nm (reference=380 nm)
Pump Parameters:

| Step | Segment Time | A | B | D | Curve |
|---|---|---|---|---|---|
| 0 | 0.5 | 80.0 | 10.0 | 10.0 | 0 |
| 1 | 3.0 | 80.0 | 10.0 | 10.0 | 0 |
| 2 | 20.0 | 0.0 | 80.0 | 20.0 | 1 |
| 3 | 5.0 | 0.0 | 80.0 | 20.0 | 0 |
| 4 | 7.0 | 80.0 | 10.0 | 10.0 | 0 |

Process Development—Catalyst Selection

Table 1 captures the experimental conditions, % conversion, and enantiomeric ratio of the asymmetric Henry reaction for conversion of 16-Br to 1-Br and 1*-Br using various chiral catalyst systems.

TABLE 1

| Entry | ligand | Cu(II) | $CH_3NO_2$ | base | solvent | Temp/time | % Conv. | e.r. 1-Br:1*-Br |
|---|---|---|---|---|---|---|---|---|
| 1 | — | — | 5 eq | $K_2CO_3$ (1.0 eq) | — | RT, 2 h | 92% | 50:50 |
| 2 | — | — | 10 eq | $Et_3N$ (0.09 eq) | EtOH | RT, 45 h | — | 50:50 |
| 3 | 17 (0.05 eq) | — | 10 eq | — | THF | RT, 23.5 h | >95% | 90:10 |
| 4 | L2 (0.1 eq) | $Cu(OTf)_2$ (0.1 eq) | 10 eq | $Et_3N$ (0.09 eq) | EtOH | RT, 70 h | 11.8% | 52:48 |
| 5 | L3 (0.1 eq) | $Cu(OTf)_2$ (0.1 eq) | 10 eq | $Et_3N$ (0.09 eq) | EtOH | RT, 70 h | <1% | 50:50 |
| 6 | L4 (0.1 eq) | $Cu(OTf)_2$ (0.1 eq) | 10 eq | $Et_3N$ (0.09 eq) | EtOH | RT, 16 h | 24% | 52:48 |
| 7 | L5 (0.1 eq) | $Cu(OTf)_2$ (0.1 eq) | 10 eq | $Et_3N$ (0.09 eq) | EtOH | RT, 70 h | 11.6% | 50:50 |
| 8 | L7 (0.1 eq) | $Cu(OTf)_2$ (0.1 eq) | 10 eq | $Et_3N$ (0.09 eq) | EtOH | RT, 16 h | No conv. | — |
| 9 | L10 (0.1 eq) | $Cu(OTf)_2$ (0.1 eq) | 10 eq | $Et_3N$ (0.09 eq) | EtOH | RT, 16 h | No conv. | — |

TABLE 1-continued

| Entry | ligand | Cu(II) | CH₃NO₂ | base | solvent | Temp/time | % Conv. | e.r. 1-Br:1*-Br |
|---|---|---|---|---|---|---|---|---|
| 10 | — | — | 10 eq | Et₃N (0.09 eq) | THF | RT, 18 h | 10.2% | 50:50 |
| 11 | — | Cu(OTf)₂ (0.1 eq) | 10 eq | Et₃N (0.09 eq) | THF | RT, 18 h | No conv. | 50:50 |
| 12 | L2 (0.1 eq) | Cu(OTf)₂ (0.1 eq) | 10 eq | Et₃N (0.09 eq) | THF | RT, 24 h: | 4.7% | 51:49 |
| 13 | L3 (0.1 eq) | Cu(OTf)₂ (0.1 eq) | 10 eq | Et₃N (0.09 eq) | THF | RT, 24 h | 3.4% | 50:50 |
| 14 | L4 (0.1 eq) | Cu(OTf)₂ (0.1 eq) | 10 eq | Et₃N (0.09 eq) | THF | RT, 24 h | 48.7% | 50:50 |
| 15 | L5 (0.1 eq) | Cu(OTf)₂ (0.1 eq) | 10 eq | Et₃N (0.09 eq) | THF | RT, 24 h | 11.6% | 50:50 |

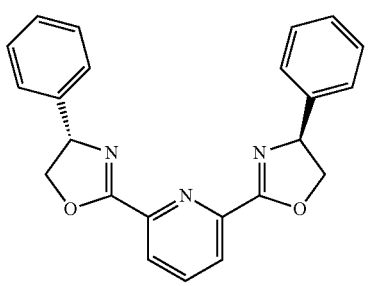

L2

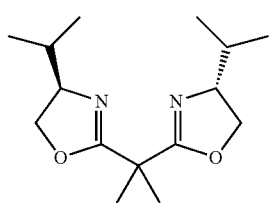

L3

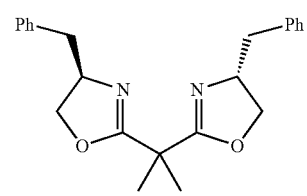

L4

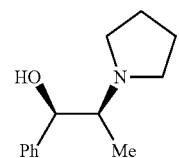

L5

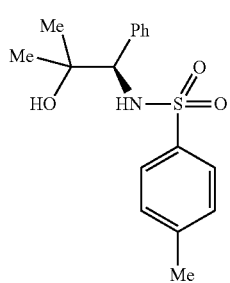

L7

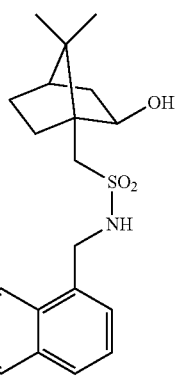

L10

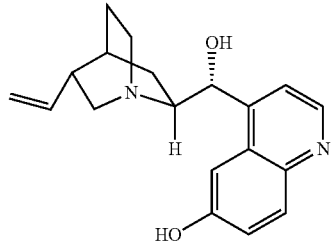

17

Asymmetric Henry reactions employing chiral ligands L2, L3, L4, L5, L7, and L10 resulted in low conversion to product and did not proceed in a stereoselective manner. However, the asymmetric Henry reaction using chiral ligand 17 provided complete conversion to product in a highly enantioselective fashion (see, Entry 3 from Table 1). Without being bound by any scientific theory, it is believed that the bicyclic structure and higher basicity of chiral ligands of Formula 3 or 3* (e.g., chiral ligand 17) may account for the increased reaction conversion and enantioselectivity when compared to the monocyclic and less basic chiral ligands L2, L3, L4, L5, L7, and L10.

Example 1

Preparation of ethyl 2-(5-bromopyridin-2-yl)-2,2-difluoroacetate (15-Br)

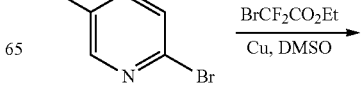

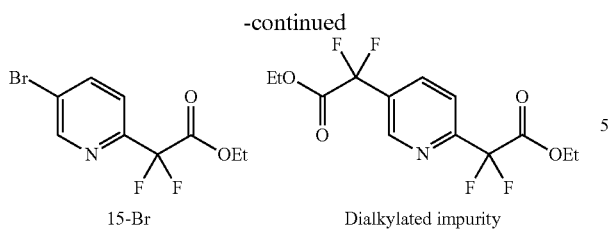

15-Br

Dialkylated impurity

In a clean multi-neck round bottom flask, copper powder (274.7 g, 2.05 eq) was suspended in dimethyl sulfoxide (3.5 L, 7 vol) at 20-35° C. Ethyl bromodifluoroacetate (449 g, 1.05 eq) was slowly added to the reaction mixture at 20-25° C. and stirred for 1-2 h. 2, 5-dibromopyridine (500 g, 1 eq) was added to the reaction mixture and the temperature was increased to 35-40° C. The reaction mixture was maintained at this temperature for 18-24 h and the reaction progress was monitored by GC.

After completion of the reaction, ethyl acetate (7 L, 14 vol) was added to the reaction mixture and stirring was continued for 60-90 min at 20-35° C. The reaction mixture was filtered through a Celite bed (100 g; 0.2 times w/w Celite and 1 L; 2 vol ethyl acetate). The reactor was washed with ethyl acetate (6 L, 12 vol) and the washings were filtered through a Celite bed. The Celite bed was finally washed with ethyl acetate (1 L, 2 vol) and all the filtered mother liquors were combined. The pooled ethyl acetate solution was cooled to 8-10° C., washed with the buffer solution (5 L, 10 vol) below 15° C. (Note: The addition of buffer solution was exothermic in nature. Controlled addition of buffer was required to maintain the reaction mixture temperature below 15° C.). The ethyl acetate layer was washed again with the buffer solution until (7.5 L; 3×5 vol) the aqueous layer remained colorless. The organic layer was washed with a 1:1 solution of 10% w/w aqueous sodium chloride and the buffer solution (2.5 L; 5 vol). The organic layer was then transferred into a dry reactor and the ethyl acetate was distilled under reduced pressure to provide crude 15-Br.

The crude 15-Br was purified by high vacuum fractional distillation and the distilled fractions having 15-Br purity greater than 93% (with the dialkylated not more than 2% and starting material less than 0.5%) were pooled together to afford 15-Br.

Yield after distillation: 47.7% with >93% purity by GC (pale yellow liquid). Another 10% yield was obtained by re-distillation of impure fractions resulting in overall yield of ~55-60%.

$^1$H NMR: δ values with respect to TMS (DMSO-$d_6$; 400 MHz): 8.85 (1H, d, 1.6 Hz), 8.34 (1H, dd, J=2.0 Hz, 6.8 Hz), 7.83 (1H, d, J=6.8 Hz), 4.33 (2H, q, J=6.0 Hz), 1.22 (3H, t, J=6.0 Hz). $^{13}$C NMR: 162.22 (t, —C=O), 150.40 (Ar—C—), 149.35 (t, Ar—C), 140.52 (Ar—C), 123.01 (Ar—C), 122.07 (Ar—C), 111.80 (t, —CF$_2$), 63.23 (—OCH$_2$—), 13.45 (—CH$_2$CH$_3$).

Example 2

Preparation of 2-(5-bromopyridin-2-yl)-1-(2,4-difluorophenyl)-2,2-difluoroethanone (16-Br)

A. One-Step Method

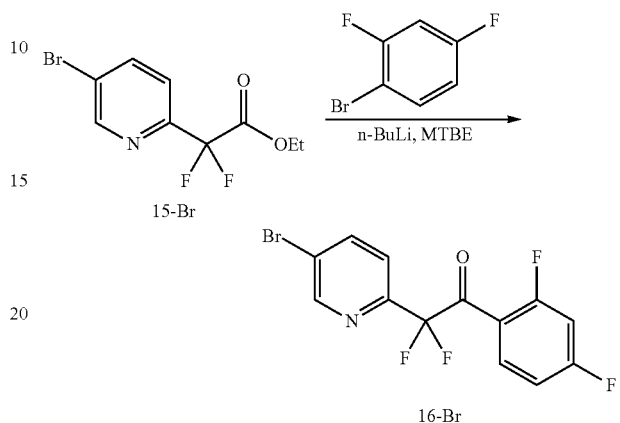

1-Bromo-2,4-difluorobenzene (268.7 g; 1.3 eq) was dissolved in methyl tert butyl ether (MTBE, 3.78 L, 12.6 vol) at 20-35° C. and the reaction mixture was cooled to −70 to −65° C. using an acetone/dry ice bath. n-Butyl lithium (689 mL, 1.3 eq; 2.5 M) was then added to the reaction mixture maintaining the reaction temperature below −65° C. (Note: Controlled addition of the n-Butyl Lithium to the reaction mixture was needed to maintain the reaction mixture temperature below −65° C.). After maintaining the reaction mixture at this temperature for 30-45 min, 15-Br (300 g, 1 eq) dissolved in MTBE (900 mL, 3 vol) was added to the reaction mixture below −65° C. The reaction mixture was continued to stir at this temperature for 60-90 min and the reaction progress was monitored by GC.

The reaction was quenched by slow addition of a 20% w/w ammonium chloride solution (750 mL, 2.5 vol) below −65° C. The reaction mixture was gradually warmed to 20-35° C. and an additional amount of a 20% w/w ammonium chloride solution (750 mL, 2.5 vol) was added. The aqueous layer was separated, the organic layer was washed with a 10% w/w sodium bicarbonate solution (600 mL, 2 vol) followed by a 5% sodium chloride wash (600 mL, 2 vol). The organic layer was dried over sodium sulfate (60 g; 0.2 times w/w), filtered and the sodium sulfate was washed with MTBE (300 mL, 1 vol). The organic layer along with washings was distilled below 45° C. under reduced pressure until no more solvent was collected in the receiver. The distillation temperature was increased to 55-60° C., maintained under vacuum for 3-4 h and cooled to 20-35° C. to afford 275 g (73.6% yield, 72.71% purity by HPLC) of 16-Br as a pale yellow liquid.

$^1$H NMR: δ values with respect to TMS (DMSO-$d_6$; 400 MHz): 8.63 (1H, d, 1.6 Hz, Ar—H), 8.07-8.01 (2H, m, 2×Ar—H), 7.72 (1H, d, J=6.8 Hz, Ar—H), 7.07-6.82 (1H, m, Ar—H), 6.81-6.80 (1H, m, Ar—H).

$^{13}$C NMR: 185.60 (t, —C=O), 166.42 (dd, Ar—C—), 162.24 (dd, Ar—C), 150.80 (Ar—C), 150.35 (Ar—C), 140.02 (Ar—C), 133.82 (Ar—C), 123.06 (Ar—C), 1122.33 (Ar—C), 118.44 (Ar—C), 114.07 (—CF$_2$—), 122.07 (Ar—C), 105.09 (Ar—C).

B. Two-Step Method Via 15b-Br

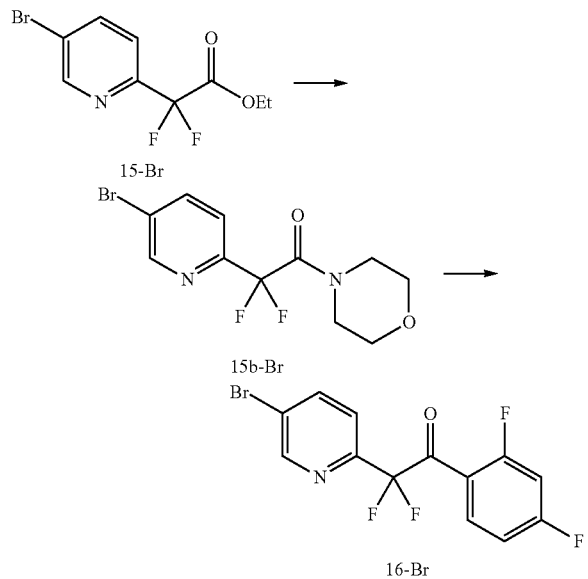

15-Br (147.0 g) was dissolved in n-heptane (1.21 L) and transferred to a 5-L reactor equipped with overhead stirrer, thermocouple, condenser and addition funnel. Morpholine (202 ml) was added. The solution was heated to 60° C. and stirred overnight. The reaction was complete by HPLC analysis (0.2% 15-Br; 94.7% 15b-Br). The reaction was cooled to room temperature and 1.21 L of MTBE was added. The solution was cooled to ~4° C. and quenched by slow addition of 30% citric acid (563 ml) to maintain the internal temperature <15° C. After stirring for one hour the layers were allowed to settle and were separated (Aq. pH=5). The organic layer was washed with 30% citric acid (322 ml) and 9% NaHCO$_3$ (322 ml, aq. pH 7+ after separation). The organic layer was concentrated on the rotary evaporator to 454 g (some precipitation started immediately and increased during concentration). After stirring at room temperature the suspension was filtered and the product cake was washed with n-heptane (200 ml). The solid was dried in a vacuum oven at room temperature to provide 129.2 g (77%) dense powder. The purity was 96.5% by HPLC analysis.

To a 1-L flask equipped with overhead stirring, thermocouple, condenser and addition funnel was added magnesium turnings (14.65 g), THF (580 ml) and 1-bromo-2,4-difluorobenzene (30.2 g, 0.39 equiv). The mixture was stirred until the reaction initiated and self-heating brought the reaction temperature to 44° C. The temperature was controlled with a cooling bath as the remaining 1-bromo-2,4-difluorobenzene (86.1 g, 1.11 equiv) was added over about 30 min. at an internal temperature of 35-40° C. The reaction was stirred for 2 hours while gradually cooling to room temperature. The dark yellow solution was further cooled to 12° C.

During the Grignard formation, a jacketed 2-L flask equipped with overhead stirring, thermocouple, and addition funnel was charged with morpholine amide 15b-Br (129.0 g) and THF (645 ml). The mixture was stirred at room temperature until the solid dissolved, and then the solution was cooled to −8.7° C. The Grignard solution was added via addition funnel over about 30 min. at a temperature of −5 to 0° C. The reaction was stirred at 0° C. for 1 hour and endpointed by HPLC analysis. The reaction mixture was cooled to −5° C. and quenched by slow addition of 2N HCl over 1 hour at <10° C. The mixture was stirred for 0.5 h then the layers were allowed to settle and were separated. The aqueous layer was extracted with MTBE (280 ml). The combined organic layers were washed with 9% NaHCO$_3$ (263 g) and 20% NaCl (258 ml). The organic layer was concentrated on the rotary evaporator with THF rinses to transfer all the solution to the distillation flask. Additional THF (100 ml) and toluene (3×100 ml) were added and distilled to remove residual water from the product. After drying under vacuum, the residue was 159.8 g of a dark brown waxy solid (>theory). The purity was approximately 93% by HPLC analysis.

Grignard Formation/Coupling Reaction 2:

Magnesium (0.022 kg, 0.903 mol), 1-bromo-2,4-difluorobenzene (0.027 kg, 0.14 mol) and tetrahydrofuran (THF) (1.4 L) were charged to a 2 L reactor fitted with a nitrogen inlet/outlet, 0.25 L dropping funnel, temperature probe and reflux condenser. After stirring for ca. 40 min at 22° C., the reaction initiated and was allowed to reach 35° C. Cooling was applied and further 1-bromo-2,4-difluorobenzene (0.153 kg, 0.79 mol) was added at 35-40° C. over 0.5 hr. On completion of the addition, the reaction was stirred at 35-40° C. for a further 1 h before cooling solution of the Grignard reagent to 20-25° C. over 1 hr. During the 1 hr cooling period, 15b-Br (0.2 kg, 0.62 mol) and THF (0.8 L) were charged to a 5 L reactor fitted with a nitrogen inlet/outlet, 0.5 L dropping funnel, temperature probe and reflux condenser and stirred at 15-20° C. to give a solution before cooling to −5 to 0° C.

The Grignard reagent was added to the solution of morpholine amide in THF at −3 to 2° C. over 50 min and the solution stirred at approximately 0° C. for 1 hr. A sample of the reaction mixture was submitted for GC analysis. A 1 ml sample was quenched into 2 M hydrochloric acid solution (5 ml) and extracted with MTBE (2 ml). The organic layer was submitted for analysis, which indicated 0.76% morpholine amide remaining.

The reaction was quenched by the addition of a 2 M hydrochloric acid solution (1 L) over 0.75 hr at less than 10° C. and stirred for a further 0.5 hr. Stirring was stopped and the phases allowed to separate. The lower aqueous layer was removed and extracted with tert-butylmethyl ether (MTBE) (0.4 L). The combined organic layers were washed with a saturated sodium hydrogen carbonate solution (0.4 L) and a saturated sodium chloride solution (0.4 L). The solvent was evaporated under vacuum at less than 50° C. and co-distilled with portions of toluene (0.2 L) until the water content by Karl Fischer (KF) analysis was less than 0.1%.

Toluene (0.37 L) and n-heptane (0.37 L) were added to the residue together with SilicaFlash P60 (40-63 micron) (0.11 kg), and the reaction stirred at 20-25° C. for 1 hr. The reaction was filtered and washed with toluene/n-heptane (1:1) (2 L). The solvent was evaporated at <50° C. and solvent swapped into THF to give an approximately 36 wt % solution of 16-Br. Gravimetric analysis of a sample of the toluene/n-heptane solution prior to evaporation indicated a mass yield of 0.21 kg (98.5%). GC assay of this material was 95.34%, to give a contained yield of 93.9%. GC (AUC) analysis of an evaporated sample was 94.5%, and HPLC (AUC) was 97.1%.

Example 3

Preparation of 1-(5-bromopyridin-2-yl)-2-(2,4-difluorophenyl)-1,1-difluoro-3-nitropropan-2-ol (1-Br or 1*-Br)

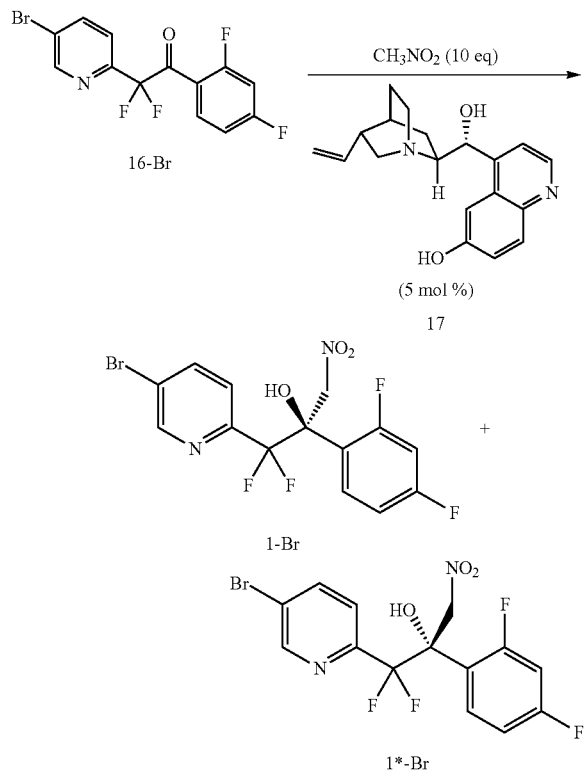

A reaction flask was charged with 16-Br (1.3 g, 3.7 mmol, 1.0 eq) and THF (3.3 mL) yielding a yellow solution. The organocatalyst 17 (59 mg, 0.19 mmol, 0.05 eq), prepared according to *J. Am. Chem. Soc.* 2012, 164, 169-172, was added to the mixture and the contents were cooled to 5° C. Subsequently, nitromethane (2.0 mL, 2.27 g, 37 mmol 10 eq) was added and the mixture was stirred at 5° C. for 23.5 h. At this point, an HPLC sample was taken to determine conversion (>95% conversion) and enantiomeric ratio (ca. 90:10 1-Br: 1*-Br). For the work up, the mixture was diluted with ethyl acetate (12 mL) and an aqueous solution of acetic acid (acetic acid 0.6 ml and water 10 ml) was added. The phases were separated and the organic phase was washed with water (8 mL) and brine (8 mL). The volatiles were removed under reduced pressure to obtain 1.15 g (75% yield) of the crude product.

$^1$H NMR: δ values with respect to TMS (DMSO-$d_6$; 400 MHz): 8.59 (1H, d, J=2.0 Hz), 7.92 (1H, dd, J=8.4 Hz, 2.3 Hz), 7.45 (1H, m), 7.34 (1H, dd, J=8.4 Hz, 2.3 Hz), 6.86-6.75 (2H, m), 5.70 (1H, d, J=12.8 Hz), 5.16 (1H, d, J=12.8 Hz).

Chiral HPLC: Retention Times: 10.97 min (1*-Br); 14.82 min (1-Br)

| HPLC Set up | |
|---|---|
| HPLC column | Chiralpak AD-H 250 mm × 4.6 mm × 5 µm |
| Column temperature | 25° C. |
| Sample temperature | 25° C. |
| Flow rate | 0.8 mL/min |
| Injection Volume | 3 µL |
| Wavelength | 215 nm |
| Run time | 20 min |
| Mobile Phase | 90 vol % n-hexane + 10 vol % 2-PrOH (isocratic) |

Example 4

Preparation of 3-amino-1-(5-bromopyridin-2-yl)-2-(2,4-difluorophenyl)-1,1-difluoropropan-2-ol (11-Br or 11*-Br)

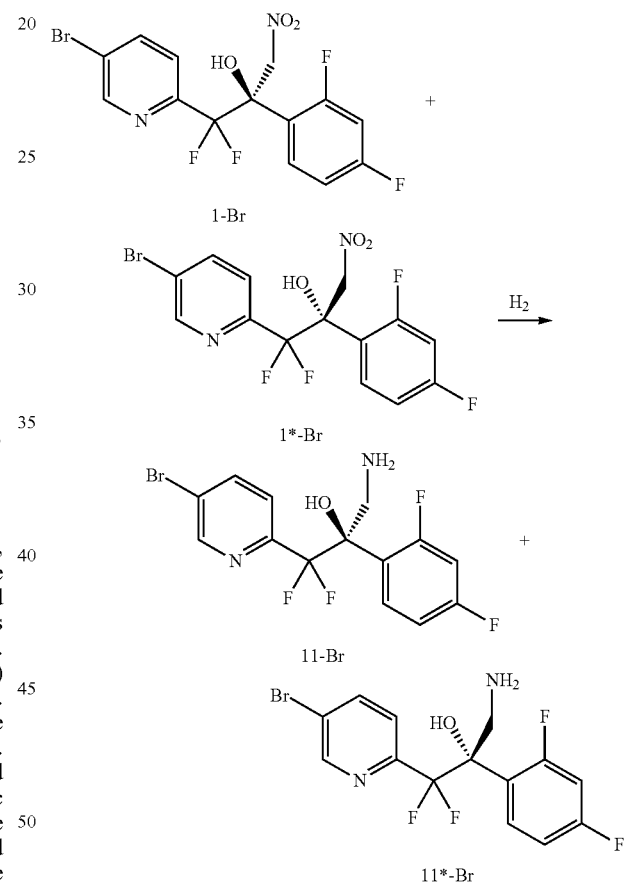

A chamber of a screening autoclave was charged with 1-Br/1*-Br (150 mg, 0.366 mmol), Noblyst® P8071[1] (ca. 0.40 mol % Pt relative to 1-Br/1*-Br) and MeOH (1.5 mL). The chamber was flushed several times with $H_2$ and pressurized to 4 bar. After 16 h, a sample was analyzed by HPLC. Upon reaction completion, the reaction mixture was filtered through a glass filter and the solvent was removed under reduced pressure to obtain the crude product.

$^1$H NMR: δ values with respect to TMS (CDCl$_3$; 400 MHz): 8.59 (1H, d, J=2.1 Hz), 7.83 (1H, dd, J=8.4 Hz, 2.2 Hz), 7.43 (1H, m), 7.24 (1H, d, J=8.4 Hz), 6.80-6.67 (2H, m), 5.20 (2H, s), 3.89 (1H, d, J=14.2 Hz), 3.47 (1H, d, J=14.2 Hz).

Achiral HPLC: Retention Times: 7.25 min (11-Br/11*-Br)

| HPLC Set up | |
|---|---|
| HPLC column | Waters x Bridge Shield RP 18 150 mm × 4.6 mm 3.5 μm |
| Column temperature | 25° C. |
| Sample temperature | 25° C. |
| Flow rate | 0.8 mL/min |
| Injection Volume | 3 μL |
| Wavelength | 254 nm |
| Run time | 18 min |
| Mobile Phase A | Water + 0.1% TFA |
| Mobile Phase B | Acetonitrile + 0.1% TFA |

| Gradient | | |
|---|---|---|
| t [min] | Mobile Phase A [vol %] | Mobile Phase B [vol %] |
| 0 min | 96 | 4 |
| 20 min | 4 | 96 |

Enantioenrichment of 11-Br/11*-Br

Di-p-toluoyl-L-tartaric acid (0.069 kg, 0.178 ml; 0.3 eq.) was charged under nitrogen to a 5 L reactor equipped with a nitrogen inlet/outlet. A solution of 11-Br/11*-Br in isopropyl alcohol (IPA, 1.718 kg; contained mass 0.225 kg, 0.59 mol; 1 eq.) was added, followed by acetonitrile (0.35 kg). The reaction mixture was stirred at approximately 20° C. and a solution resulted. The reaction was heated to 50-55° C. (target 52° C.) and stirred at this temperature for 4 hr, during which time a precipitate resulted. An in-process chiral HPLC sample of the reaction was taken by hot filtration of the sample and washing with IPA/acetonitrile (4:1). This indicated a chiral purity of >99%.

The reaction was allowed to cool and stir at 20-25° C. over 16 hr. A second sample was submitted for chiral HPLC analysis, which indicated 99.5% purity. The reaction mixture was filtered and washed with a mixture of IPA/acetonitrile (4:1) (0.84 L). The resulting solid was dried under vacuum at 50° C. to give 11-Br hemi L-DTTA salt (0.113 kg) as a white solid. The mass yield was 33.2%, which is 66.35% of the desired isomer. Chiral HPLC indicated 99.6% purity, and achiral HPLC indicated 99.7% purity.

Neutralization of 11-Br Hemi L-DTTA Salt

11-Br hemi L-DTTA salt (250 g, 0.437 mol) was charged to a 3-necked flask equipped with overhead stirrer, nitrogen inlet, dropping funnel and thermocouple. The solid was suspended in MTBE (1.25 L). A 10% $K_2CO_3$ aq. solution was added slowly at room temperature (slightly exothermic) with stirring. After complete addition, the biphasic mixture was stirred for 10 minutes until all solid dissolved. The aqueous layer was separated and extracted with another 0.625 L of MTBE. The combined organic layers were concentrated on a rotary evaporator under vacuum. The residue was diluted in toluene (0.30 L) and concentrated again to provide a syrup residue of 11-Br (169.7 g). The procedure was repeated twice more starting with 250 g and 243 g, respectively, of 11-Br hemi L-DTTA salt.

Example 5

Preparation of 1-(5-bromopyridin-2-yl)-2-(2,4-difluorophenyl)-1,1-difluoro-3-(1H-tetrazol-1-yl)propan-2-ol (13-Br or 13*-Br)

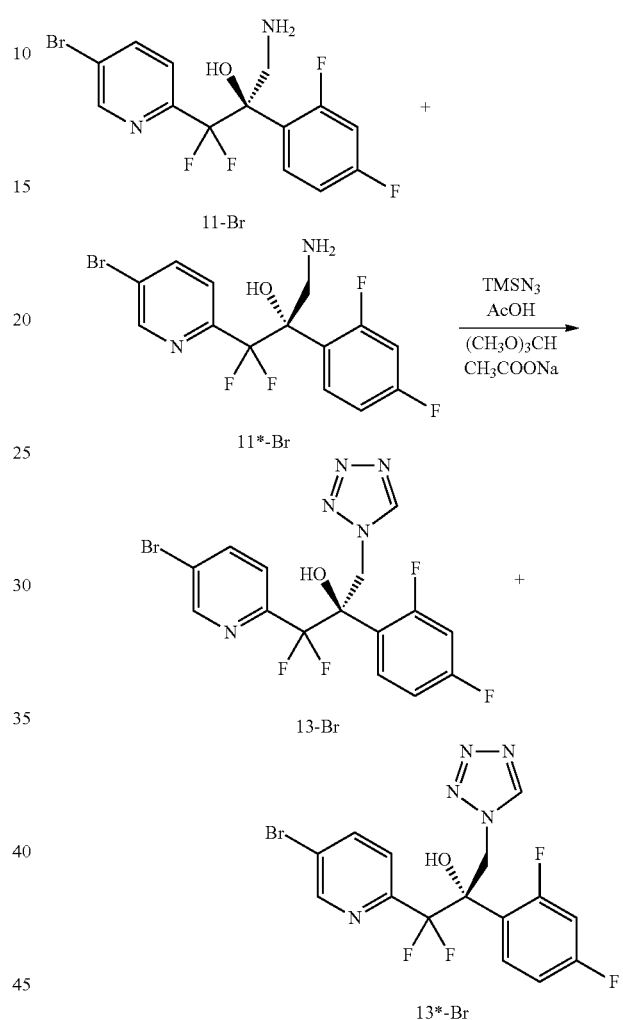

11-Br/11*-Br (20.0 g, 1 eq.) was added to acetic acid (50 mL, 2.5 vol) at 25-35° C. followed by the addition of anhydrous sodium acetate (4.32 g, 1 eq) and trimethyl orthoformate (15.08 g, 2.7 eq). The reaction mixture was stirred for 15-20 min at this temperature and trimethylsilyl azide (12.74 g, 2.1 eq) was added to the reaction mixture (Chilled water was circulated through the condenser to minimize the loss of trimethylsilyl azide from the reaction mixture by evaporation). The reaction mixture was then heated to 70-75° C. and maintained at this temperature for 2-3 h. The reaction progress was monitored by HPLC. Once the reaction was complete, the reaction mixture was cooled to 25-35° C. and water (200 mL, 10 vol) was added. The reaction mixture was extracted with ethyl acetate (400 mL, 20 vol) and the aqueous layer was back extracted with ethyl acetate (100 mL, 5 vol). The combined organic layers were washed with 10% potassium carbonate solution (3×200 mL; 3×10 vol) followed by a 10% NaCl wash (1×200 mL, 10 vol). The organic layer was distilled under reduced pressure below 45° C. The crude product obtained was azeotroped with heptanes (3×200 mL) to provide 21.5 g (94% yield, 99.26% purity) of the tetrazole 13-Br/13*-Br compound as a pale brown solid (low melting solid).

$^1$H NMR: δ values with respect to TMS (DMSO-d$_6$; 400 MHz NMR instrument): 9.13 (1H, Ar—H), 8.74 (1H, Ar—H), 8.22-8.20 (1H, m, Ar—H), 7.44 (1H, d, J=7.2 Hz, Ar—H), 7.29 (1H, Ar—H), 7.23-7.17 (1H, m, Ar—H), 6.92-6.88 (1H, Ar—H), 5.61 (1H, d, J=11.2 Hz, —OCH$_A$H$_B$—), 5.08 (1H, d, J=5.6 Hz, —OCH$_A$H$_B$—).

$^{13}$C NMR: 163.67-161.59 (dd, Ar—C—), 160.60-158.50 (dd, Ar—C—), 149.65 (Ar—C), 144.99 (Ar—C), 139.75 (Ar—C), 131.65 (Ar—C), 124.26 (Ar—C), 122.32 (d, Ar—C), 119.16 (t, —CF$_2$—), 118.70 (d, Ar—C), 111.05 (d, Ar—C) 104.29 (t, Ar—C), 76.79 (t, —C—OH), 59.72 (Ar—C), 50.23 (—OCH$_2$N—).

Alternative Procedure for the Synthesis of 13-Br/13*-Br

11-Br/11*-Br (76.6 g, theoretically 33.1 g contained 11-Br, 87.4 mmol) was transferred to a pressure bottle. Glacial acetic acid (117 g, 0.1% water by KF analysis), sodium acetate (7.18 g, 87.6 mmol, 1 equiv, 0.44% water by KF analysis), and trimethylorthoformate (55.75 g, 525 mmol, 6 equiv, 0.02% water by KF analysis) were added and the mixture was stirred under nitrogen at room temperature for 2 hours (during this time trimethylorthoformate reacts off any residual moisture in the system prior to starting the reaction). Trimethylsilyl azide (18.5 ml, 131 mmol, 1.5 equiv) was added all at once. The pressure bottle was sealed and heated in an oil bath at 67° C. overnight (16 h), then cooled and sampled for completion (No 11-Br/11*-Br was detected. The expected byproduct of an incomplete reaction, the formamide of 11-Br/11*-Br, if present, was very small.). The reaction mixture was diluted with 2-MeTHF (332 ml) and a total of 312 ml of water (232 mL of water was added initially, and later 80 mL was added when some precipitate formed, presumably sodium acetate, during the cold neutralization.). The mixture was cooled to 0° C. and neutralized by slow addition of 50% NaOH (exothermic, added at a rate to maintain the internal temperature <25° C.). A total of 177 g 50% NaOH brought the pH to 10. After warming to 25° C. the layers were settled and separated. The organic product phase was washed with 10% aqueous potassium carbonate (181 g)–Aq. pH=>10. The organic layer was washed with 20% aqueous sodium chloride (191 g)–Aq. pH=≥7.

For scale up, the organic layer can be concentrated under vacuum and dried by additional distillations of 2-MeTHF with a final target volume of 5 mL 2-MeTHF per gram theoretical 13-Br/13*-Br and target water content <0.1%. During the distillations the solution was polish-filtered to remove a small amount of inorganic solid that was observed.

Example 6

Preparation of 4-((4-((6-(2-(2,4-difluorophenyl)-1,1-difluoro-2-hydroxy-3-(1H-tetrazol-1-yl)propyl)pyridin-3-yl)ethynyl)phenoxy)methyltbenzonitrile (5 or 5*)

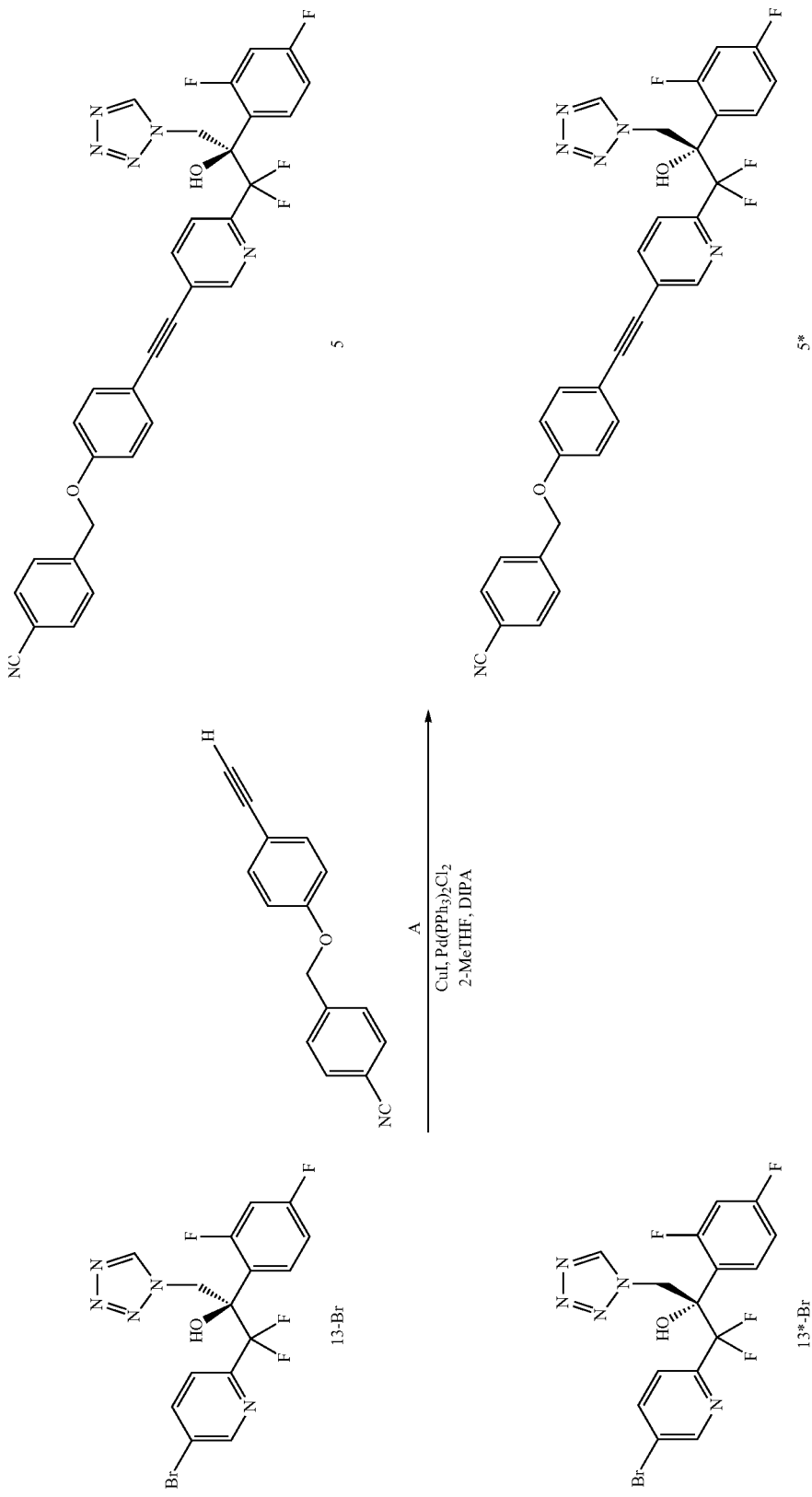

To a round bottom flask equipped with overhead stirrer, dropping funnel, nitrogen inlet and thermocouple was charged 13-Br/13*-Br (47.4 g, 110 mmol, 1 equiv.). A total of 237 ml of 2-MeTHF (5 vol) was added to dissolve and transfer the residue to the reaction flask. Diisopropylamine (236 ml, 5 vol), compound A (27.38 g, 117.4 mmol, 1.07 equiv.) and CuI (0.21 g, 1.1 mmol, 1 mol %) were added. The mixture was sparged with nitrogen for 11 min. Pd(PPh$_3$)$_2$Cl$_2$ (0.385 g, 0.5 mol %) was added, and the mixture was again sparged with nitrogen for 6 minutes. The reaction mixture was heated to 50° C. and stirred overnight. After 24 h the reaction was complete by HPLC analysis as described in the table below.

| Time | 13-Br/13*-Br (A %) | compound A (A %) | 5/5* (A %) |
|---|---|---|---|
| 4 h | 4.1 | 3.3 | 90.4 |
| 8 h | 2.0 | 1.5 | 93.6 |
| 24 h | 0.8 | 1.2 | 95.8 |

The reaction mixture was cooled to room temperature. Celite 545 (5.2 g) was added, followed by slow addition of water (237 mL, 5 vol) and the biphasic mixture was stirred for ½ hour. The mixture was filtered with a rinse of 2-MeTHF (50 mL, 1 vol) and the layers were settled. The aqueous layer (241 g, pH 11-12) was removed. The upper product layer was diluted with 2-MeTHF (200 mL, 4 vol) and stirred with a 10% aqueous solution of disodium EDTA dihydrate (247 g) for 5 hours at room temperature. The layers were settled and separated (aqueous 254 g, pH 12, blue in color). The upper organic layer was stirred with 10% aqueous N-acetyl cysteine solution (237 mL) at 50° C. for 22 h. After cooling to room temperature, the layers were settled (slow) and separated. The aqueous layer was drained (287 g, pH 10-11). The upper organic layer was stirred again with 10% aqueous N-acetyl cysteine solution (238 g) at 50° C. for 22 h. After cooling to room temperature, the layers were settled (slow) and separated. The aqueous layer was removed (277 g, pH 10).

The resulting dark amber organic layer (460 g) was sampled for Pd and Cu analysis (results in the table below) and concentrated to about ½ volume. 2-MeTHF was added and concentrated to about ½ volume. 2-MeTHF was added again and concentrated to 295 g solution. A total of about 482 g of solvent was removed by distillation. The water content of the final solution was 0.55% by KF analysis. NMR analysis indicated that the majority of diisopropylamine was removed.

The solution was divided into two equal portions. One-half was treated with SSI Si-DMT metal scavenger (3.2 g, 10% based on theoretical yield of 5/5*) and Darco G-60 carbon (6.4 g, 20% based on theoretical yield of 5/5*). The other half was treated with Phosphonics STA3 metal scavenger (3.2 g) and Darco G-60 carbon (6.4 g). Both portions were stirred at 50° C. for 20-21 hours. Both portions were then separately filtered through a glass fiber filter and a 1 micron PTFE membrane with 2-MeTHF rinses (about 35 g each). Both filtrates were sampled for Pd and Cu analysis (results in the table below).

| Sample | Cu (ppm) | Pd (ppm) |
|---|---|---|
| After N-Acetyl cysteine washes | <3.7 | 287 |
| SSI Si-DMT + Darco treatment | <3.7 | 49 |
| Phosphonics STA3 + Darco treatment | <2.5 | 70 |

The filtrates were combined for a total of 345 g solution. The solution was partially concentrated and solvent exchanged into toluene with repeated additions of toluene (total 643 g) and partial concentration to a final toluene solution weight of 268.5 g (theoretically 64.1 g of 5/5* and 236 mL of toluene). NMR analysis indicated no diisopropylamine remained and about 1% of 2-MeTHF)

The mixture was allowed to crystallize while stirring overnight. The suspension was heated to 55-60° C. until a very thin suspension remained and then was slow cooled at 1° C./h overnight (If the mixture is cooled too fast, the product may precipitate into a "pudding" consistency. Once a good suspension forms it can be cooled more quickly to isolation temperature.). The next day the suspension was cooled in an ice-bath at ca. 10° C. for 3.5 hours. The product was collected on a vacuum filter and rinsed with cold toluene (50 mL in portions). The wet cake was dried in a vacuum oven at 40-50° C. to provide 45.2 g (70.6% overall yield) of 5/5* as a beige-colored powder. The purity was 99.2 A % by the API HPLC analysis method.

Example 7

Sulfonic Acid Salt Formation of 5 or 5*

Salt formation of compound 5 was investigated with three sulfonic acids: methylsulfonic acid (MsOH), p-toluenesulfonic acid (TsOH), and benzenesulfonic acid (BsOH). Salt formation of 5 with MsOH was not achieved in a variety of solvents (iPrOAc, MIBK, EtOH, toluene, DCM, MeOH, MTBE, and anisole). However, salt formation of 5 with BsOH and TsOH in isopropyl acetate provided crystalline forms of the respective salts. Compound 5 (15 g) was dissolved in 10 vol of isopropyl acetate with slight warming. The sulfonic acids (1 equiv) were added at room temperature and stirred for 1-1.5 h to provide a coarse suspension. The suspensions were heated to about 60° C., resulting in suspensions of fine particles that were stirred overnight at room temperature and isolated at room temperature. The salts were then dried under vacuum at about 40° C. Properties of the respective salts are shown in Table 2. Dynamic vapor sorption (DVS) analysis was carried out on these two salts (FIGS. 1 and 2), and the tosylate salt was surprisingly found to have improved properties over the besylate salt. In particular, the besylate salt was hygroscopic as evidenced by the sharp weight gain between 55 and 60% RH (FIG. 2), which indicates likely hydrate formation.

TABLE 2

| Acid | Yield (%) | Purity by i-p HPLC (A %) | Purity by API HPLC (A %)[1] | M.P. by DSC (° C. peak) | Particle size, μm (D50) |
|---|---|---|---|---|---|
| BsOH | 84 | 98.5 | 94.8 | 159.7 | 20 |
| TsOH | 81 | 98.5 | 97.9 | 157.8 | 10 |

Example 8

Preparation of 4-((4-(6-(2-(2,4-difluorophenyl)-1,1-difluoro-2-hydroxy-3-(1H-tetrazol-1-yl)propyl)pyridin-3-yl)ethynyl)phenoxy)methyl)benzonitrile 4-methylbenzenesulfonate (14 or 14*)

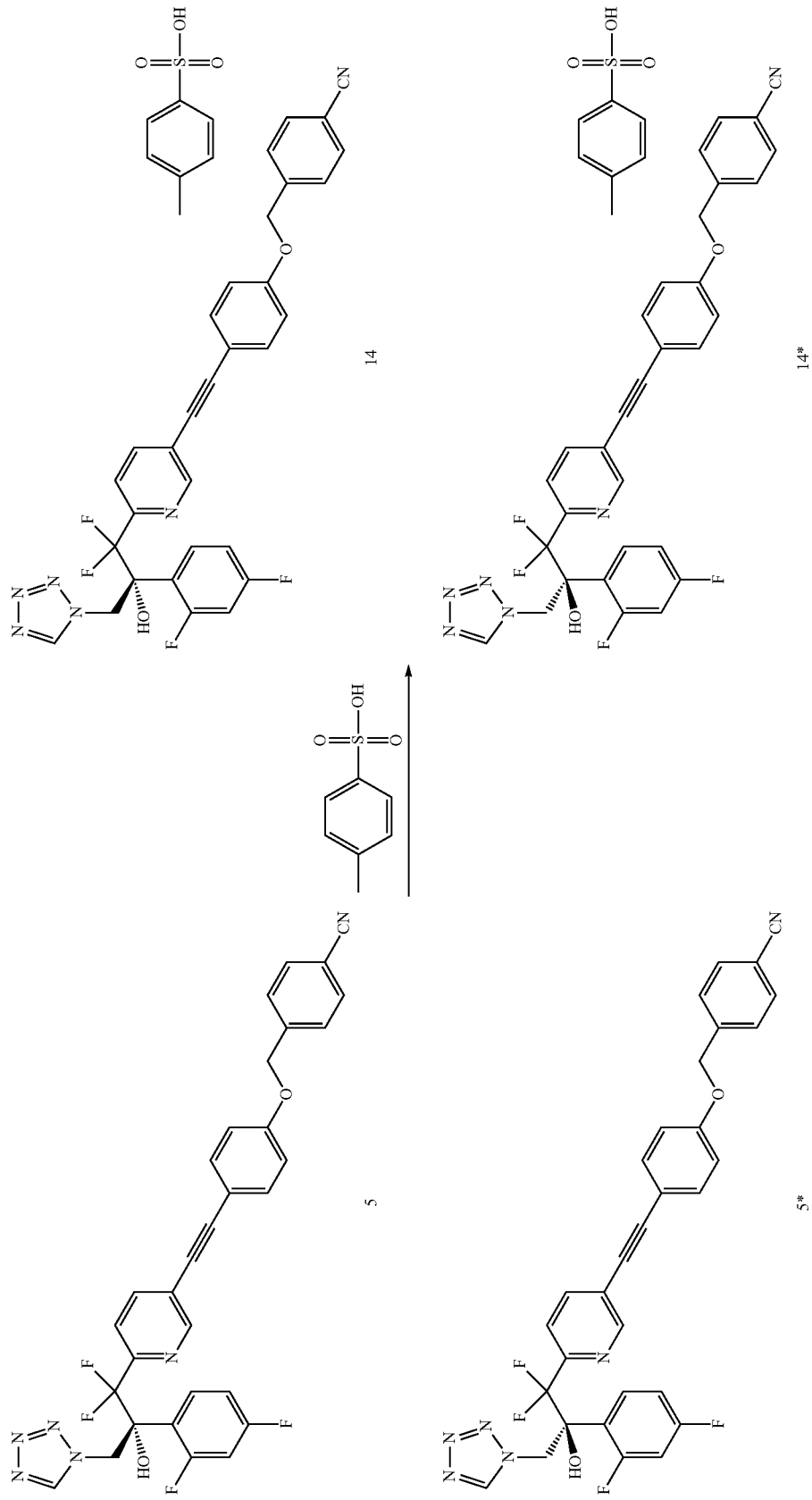

Figure 2:
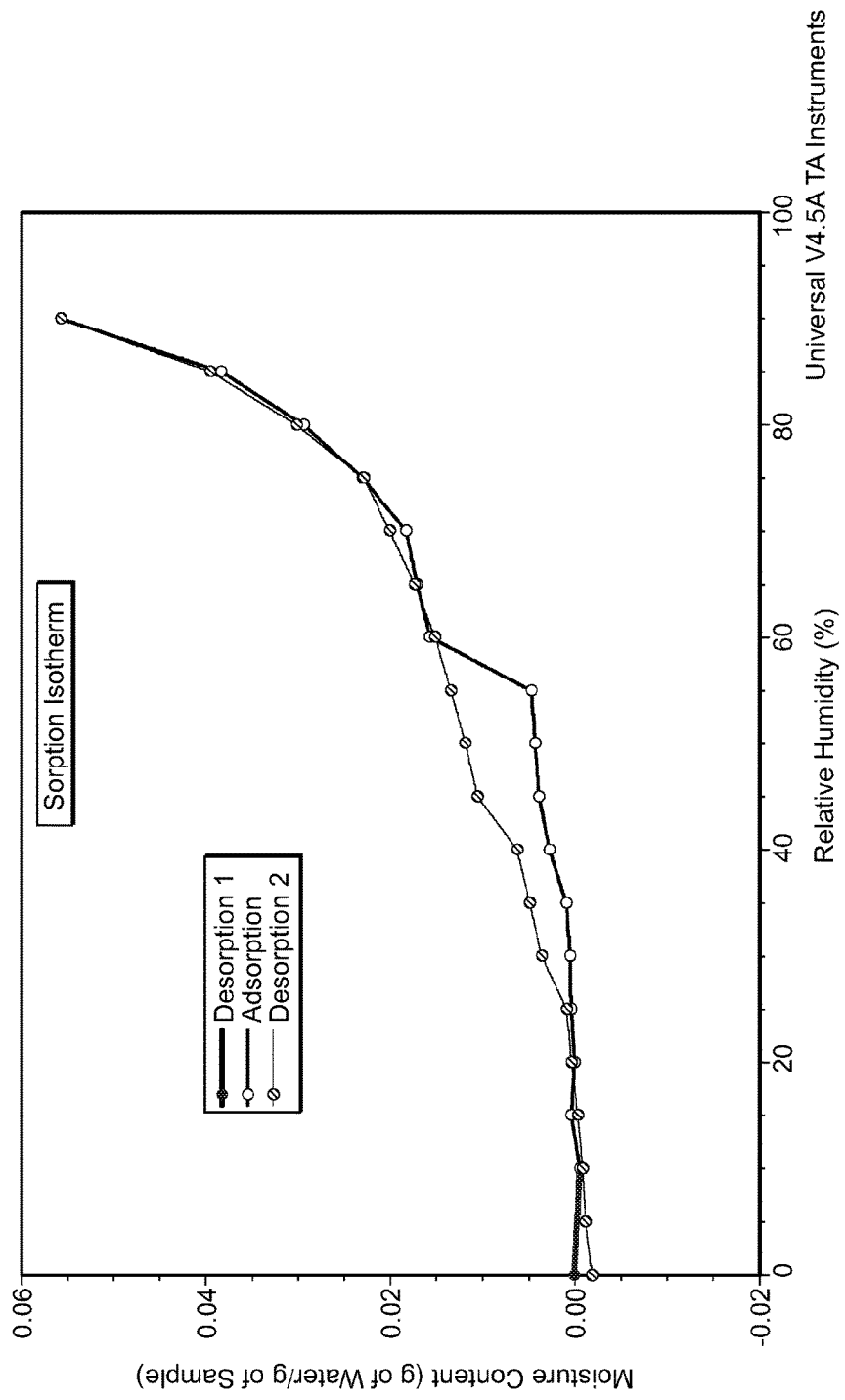
FIG. 2: depicts a DVS analysis of a benzensulfonic acid salt of compound 5.
Figure 3:
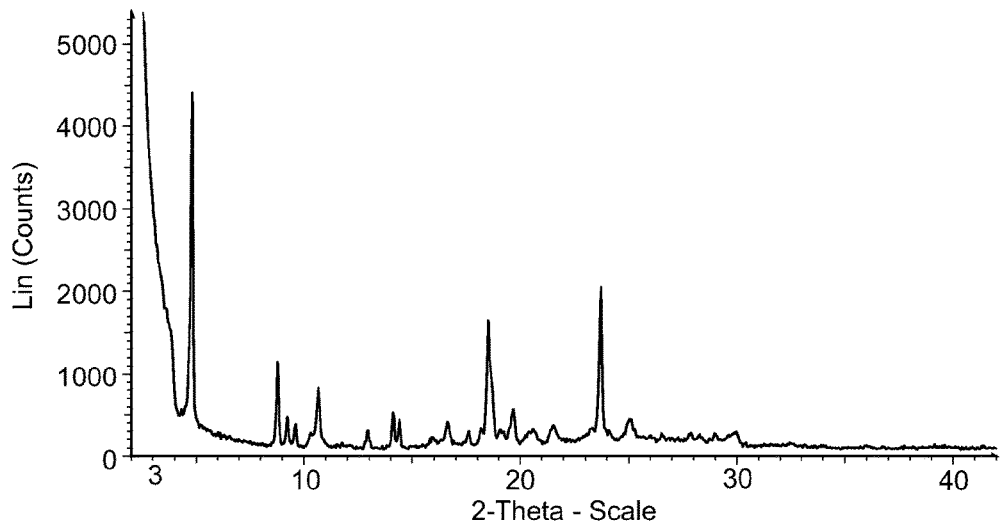
FIG. 3: depicts an XRPD pattern of an anhydrous form of compound 14 (Form 1).
Figure 4:
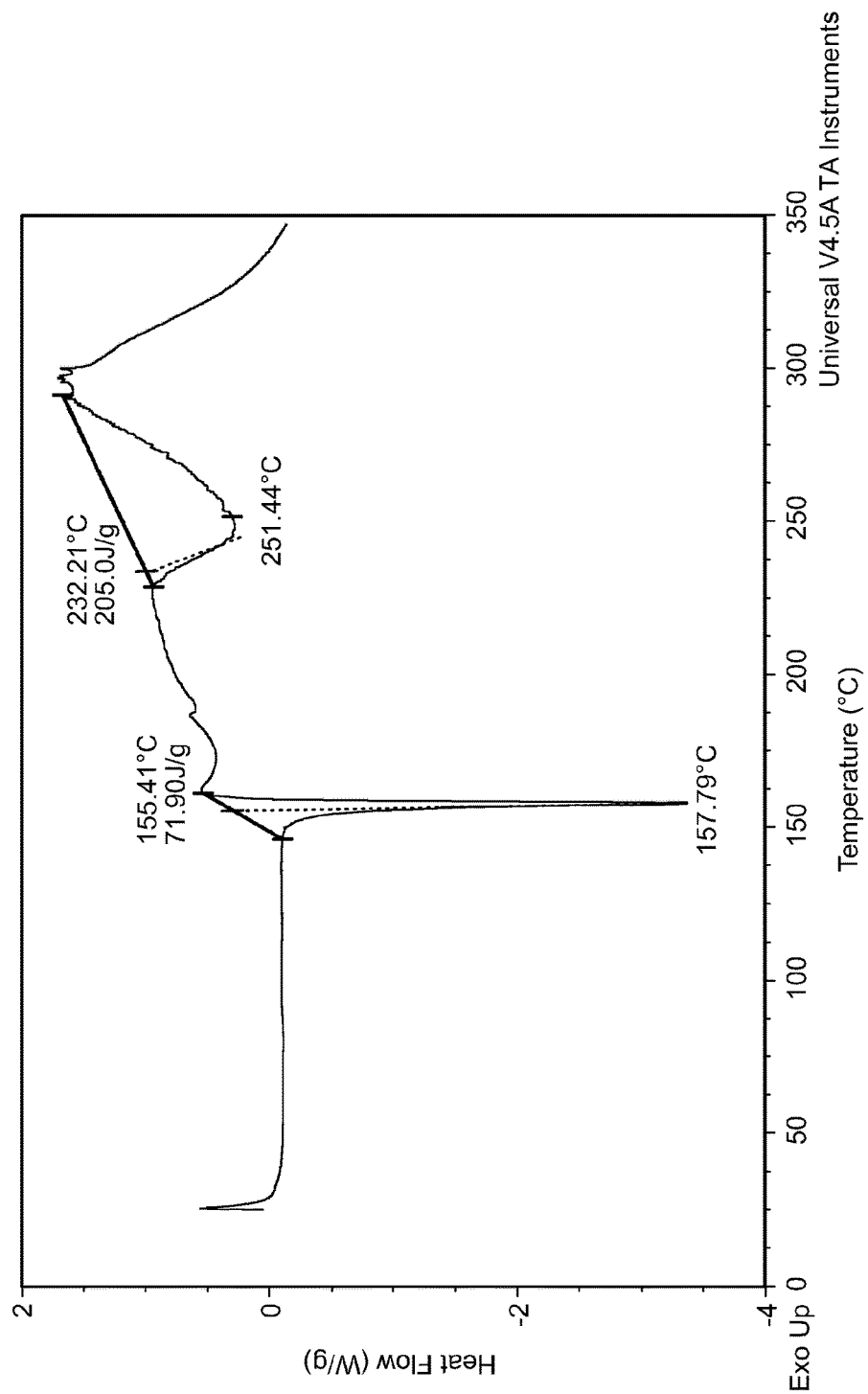
FIG. 4: depicts a DSC thermogram of an anhydrous form of compound 14 (Form 1).
Figure 5:
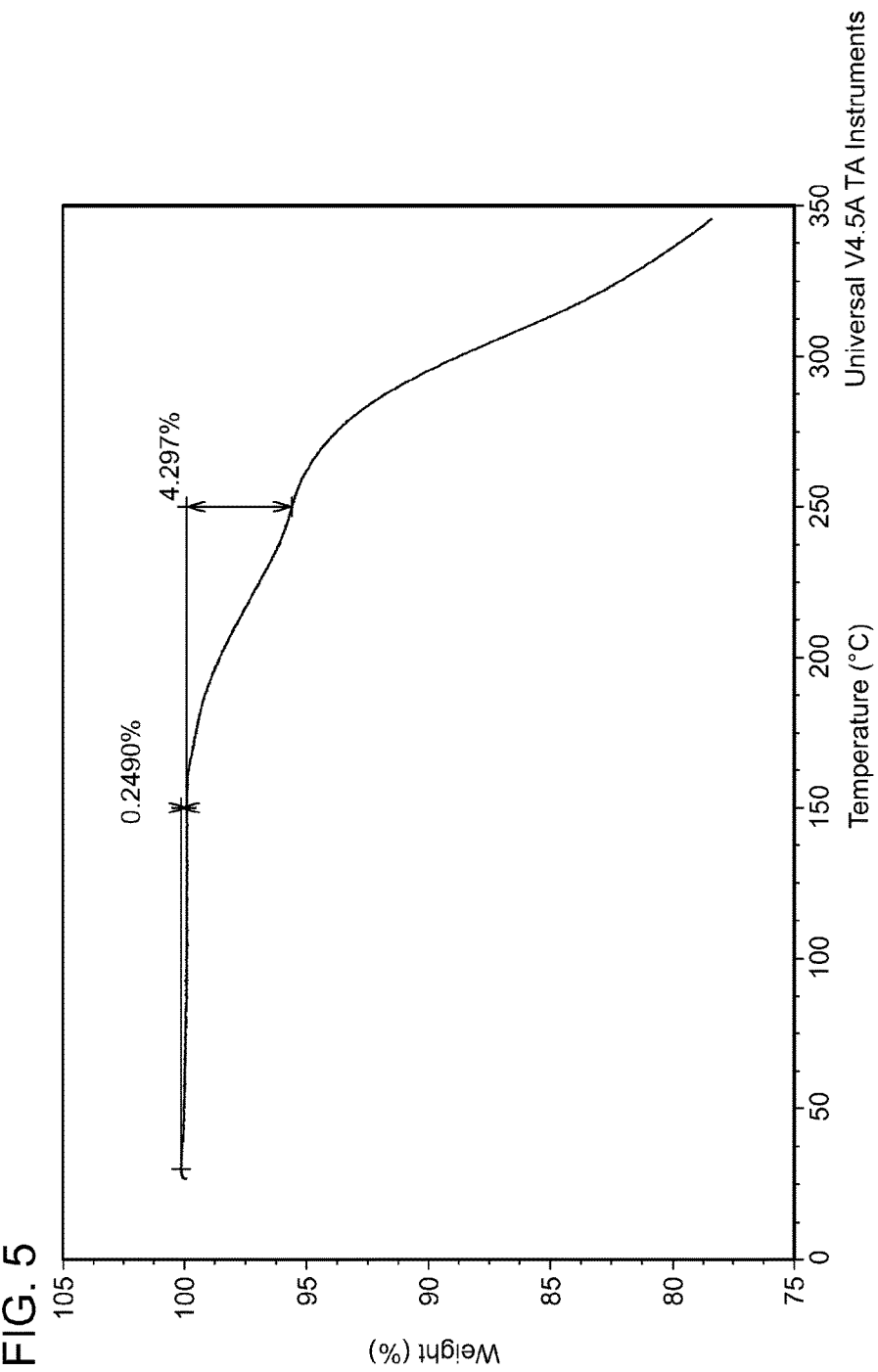
FIG. 5: depicts a TGA thermogram of an anhydrous form of compound 14 (Form 1).

5/5* (15 g, 25.7 mmol) was suspended in isopropyl acetate (120 ml, 8 vol) and warmed to 30° C. para-Toluenesulfonic acid monohydrate (4.88 g, 25.7 mmol, 1 equiv) was added and the mixture was heated to 50-60° C. until a uniform suspension was obtained (Initially a coarse clumpy suspension formed that over time (~1 hr) converted to a uniform suspension of fine particles.). The suspension was cooled and stirred overnight at room temperature and then in an ice-bath for several hours. The product was isolated on a vacuum filter and washed with cold isopropyl acetate (15 ml). The wet cake was dried in a vacuum oven at 50° C. to provide 16.7 g (86% yield) of the title compound as a beige powder. By XRPD, the product was determined to be to be an anhydrous polymorph (Form 1; FIG. 3) with a melt onset at 155° C. (FIG. 4). It was stable after 7 days storage at elevated humidity conditions. The sample was slightly hygroscopic by GVS with a moisture uptake of ~1.6% at 90% RH (FIG. 1).

Example 9

Preparation of 4-((4-ethynylphenoxy)methyl)benzonitrile (A)

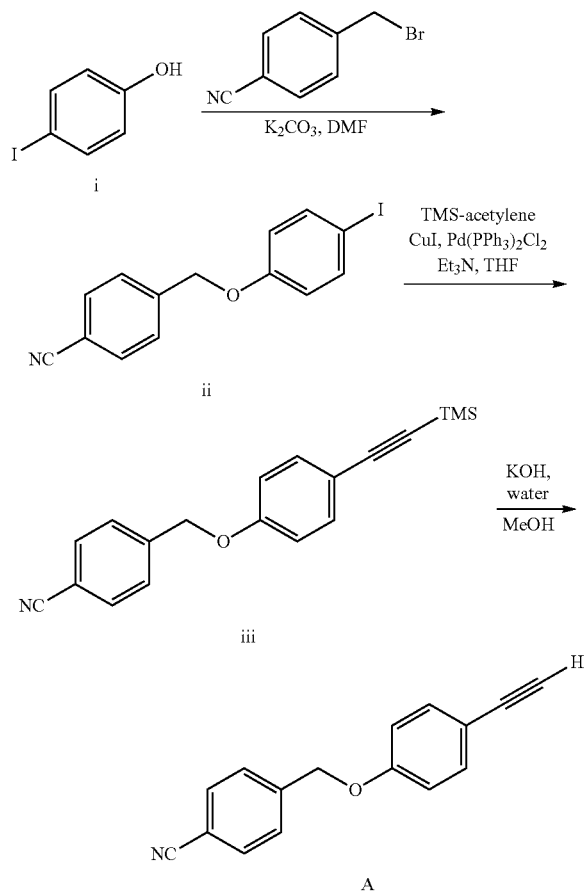

4-((4-Iodophenoxy)methyl)benzonitrile (ii)

4-Iodophenol (1.745 kg, 7.93 mol) was charged to a 50-L half-jacketed flask equipped with overhead stirrer, nitrogen inlet, thermocouple and addition funnel. DMF (17.5 L) was added and stirred at 20° C. until all of the solid dissolved. The solution was cooled to −3.5° C. Powdered $K_2CO_3$ (2.18 kg, 15.8 mol, Sigma-Aldrich −325 mesh powder, catalog number 347825) was added and the suspension was stirred vigorously for 3 hours at about −1° C. The mixture was cooled to −2.5° C. and 4-(bromomethyl)benzonitrile (1.48 kg, 7.55 mol) was added. After stirring for 1 hour at about 0° C. the mixture was allowed to warm and stir overnight at 25° C. A sample was taken for analysis. In-process HPLC analysis showed complete disappearance of 4-(bromomethyl)benzonitrile. The reaction mixture was cooled to 10° C. and quenched by slow addition of cold water (18 L) over 25 minutes (maximum temperature was 22° C. during addition). The suspension was stirred for 2 hours at room temperature, then the product was isolated by vacuum filtration and allowed to dry overnight on the vacuum filter (filtrate=38.0 kg). The solid was charged back to the reactor and suspended in deionized water (18 L) for 1.2 hours. The product was isolated by vacuum filtration and allowed to dry on the vacuum filter for 2 hours (filtrate=19.6 kg). (The second vacuum filtration can be replaced by two water washes of 2.5 vol each.) The wet cake (3827 g) was dried in a vacuum oven at 50° C. to a constant weight (4 days) of 2476.5 g (97.9%). The purity was 100 A % by in-process HPLC analysis.

4-((4-ethynylphenoxy)methyl)benzonitrile (A)

4-((4-Iodophenoxy)methyl)benzonitrile (ii) (100 g, 298 mmol) and CuI (571 mg, 1 mol %) were charged to a nitrogen-flushed 3-L round bottom flask equipped with overhead stirrer, addition funnel, nitrogen inlet and thermocouple. Dry THF (500 mL, 5 vol) and triethylamine (204 ml, 2 vol) were added and stirred to form a greenish solution. The solution was cooled to a target of 0° C. Trimethylsilyl acetylene (42.0 g, 428 mmol, 1.43 equiv) was added and the resulting thin greenish suspension was sparged with nitrogen for 11 minutes. $Pd(PPh_3)_2Cl_2$ (421 mg, 0.2 mol %) was added and the mixture was sparged with nitrogen for 10 minutes. The temperature was −7° C. after sparging. The cooling bath was removed and the mixture slowly warmed over 1.3 h to 23.5° C. during which time it became a yellow solution with some suspended solid. The reaction was stirred overnight at this temperature. After 14 h, in-process HPLC analysis showed appearance of 4-((4-((trimethylsilyl)ethynyl)phenoxy)methyl)benzonitrile (iii), and complete disappearance of 4-((4-iodophenoxy)methyl)benzonitrile (ii).

Separately, a solution of 45% KOH (75.0 g, 613 mmol, 2.06 equiv), water (38.1 g) and methanol (310 ml/243 g) was prepared. This solution was cooled to <10° C. and sparged with nitrogen for 14 minutes.

The mixture containing 4-((4-((trimethylsilyl)ethynyl)phenoxy)methyl)benzonitrile (iii) was cooled to 5° C. and the KOH/methanol/water solution was added slowly over 17 minutes to a final temperature of 10° C. The resulting brown thin suspension was allowed to warm and after about 1 hour the reaction was complete by in-process HPLC analysis (0.8% of iii detected). The mixture was cooled and deionized water (866 g total) was added slowly at 10-14° C., resulting in precipitation of A. After 2.8 hours stirring cold, the product was isolated on a vacuum filter (6° C.). The wet cake was washed with 5:1 (v/v) water/THF (2×600 mL) and then water (2×200 mL). The wet cake was dried in a vacuum oven at 40° C. to provide 66.5 g of the title compound as a brown powder (95.5% yield overall from ii). The purity was 99.5 A % by the in-process HPLC method.

Example 10

Compound 5/5* Anhydrous Form 1 Preparation

Figure 6:
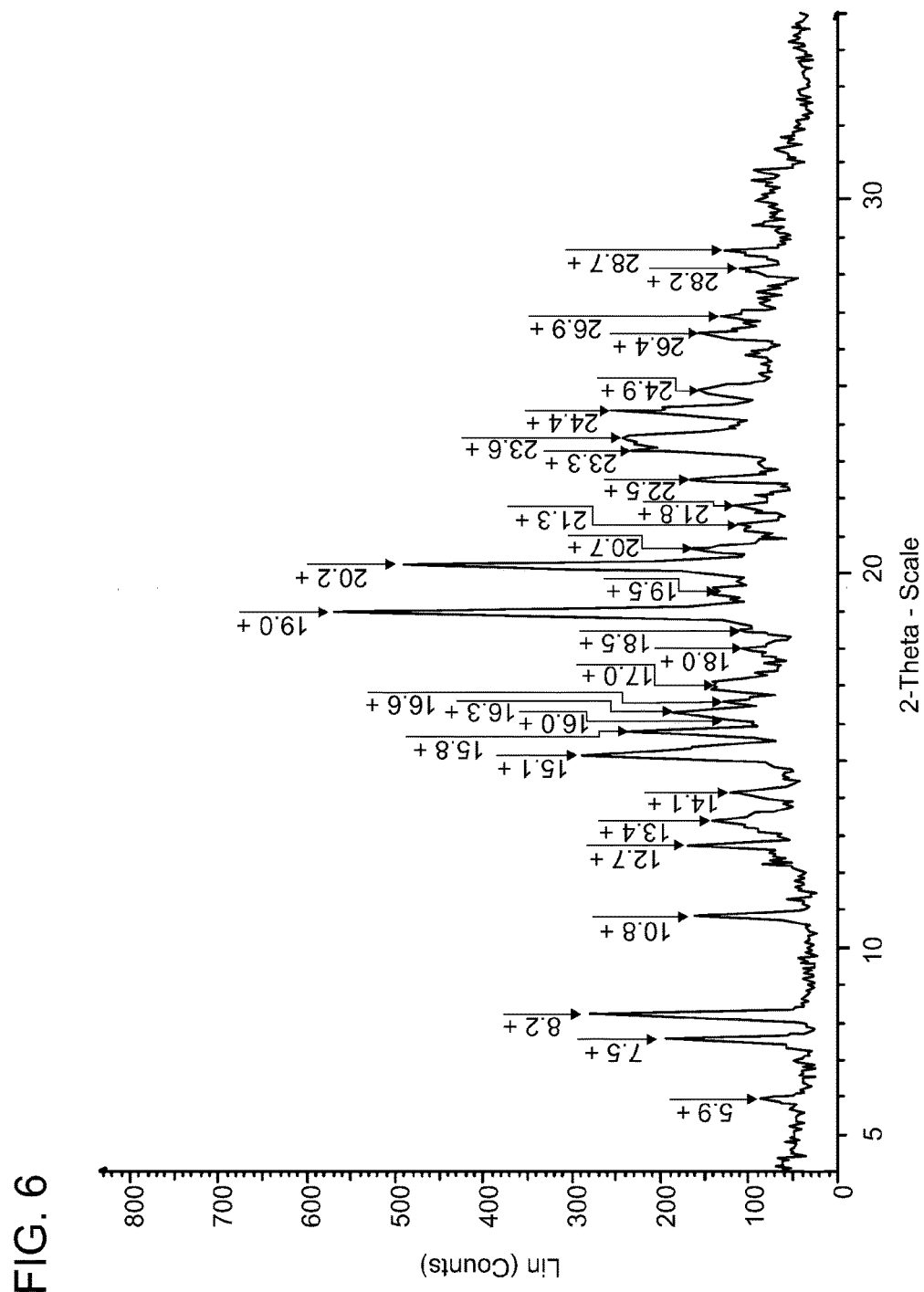
FIG. 6: depicts an XRPD pattern of an anhydrous form of compound 5 (Form 1).
Figure 7:
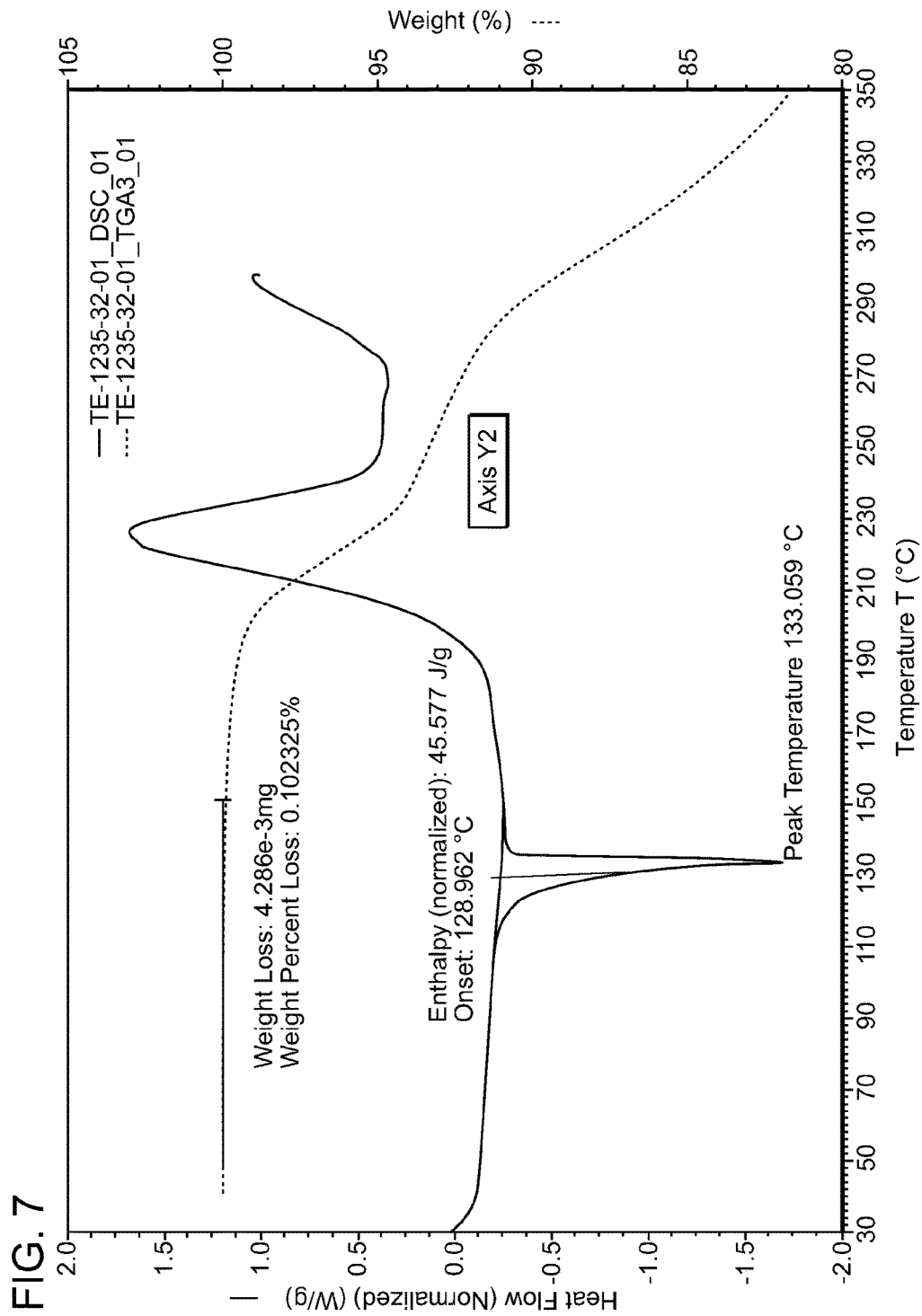
FIG. 7: depicts DSC and TGA thermograms of an anhydrous form of compound 5 (Form 1).

Amorphous compound 5 (500 mg) was suspended in heptane:acetone (40:1, 10 mL) and stirred at 50-55° C. for 5 days. Additional solvent was added on day 4 (125 µl acetone+3 mL heptane). The mixture was filtered under suction and dried at 115° C. for 4 hours to provide 340 mg of a single phase of Form 1 (FIG. 6). Form 1 was determined to be an anhydrous polymorph form with a melt onset at 129° C. (FIG. 7). Form 1 was stable after 7 days storage at elevated humidity conditions. The sample was slightly hygroscopic by GVS with a moisture uptake of ~1.3% at 90% RH.

Example 11

Compound 5/5* Anhydrous Form 2 Preparation

Figure 8:
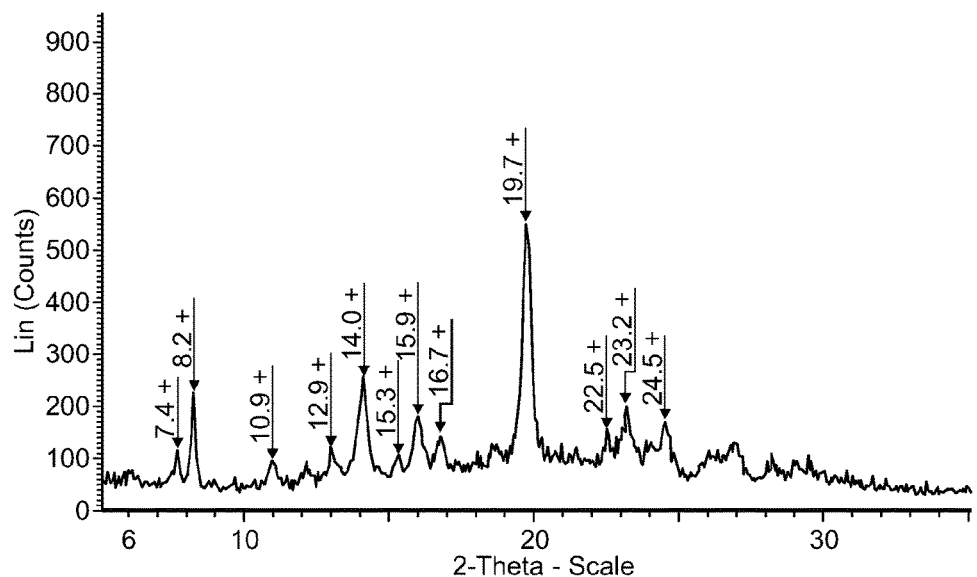
FIG. 8: depicts an XRPD pattern of an anhydrous form of compound 5 (Form 2).

Amorphous compound 5 (500 mg) was suspended in isopropyl alcohol (IPA) (10 mL) and stirred at 5° C. for 5 days followed by 30° C. for 1 day. Additional solvent was added on day 4 (5 mL IPA). The mixture was filtered under suction and dried at 25° C. for 4 hours to provide 320 mg of Form 2 (FIG. 8). Form 2 was an anhydrous form that remained stable after 7 days storage at elevated humidity conditions. The sample was slightly hygroscopic by GVS with a moisture uptake of ~0.7% at 90% RH.

Figure 9:
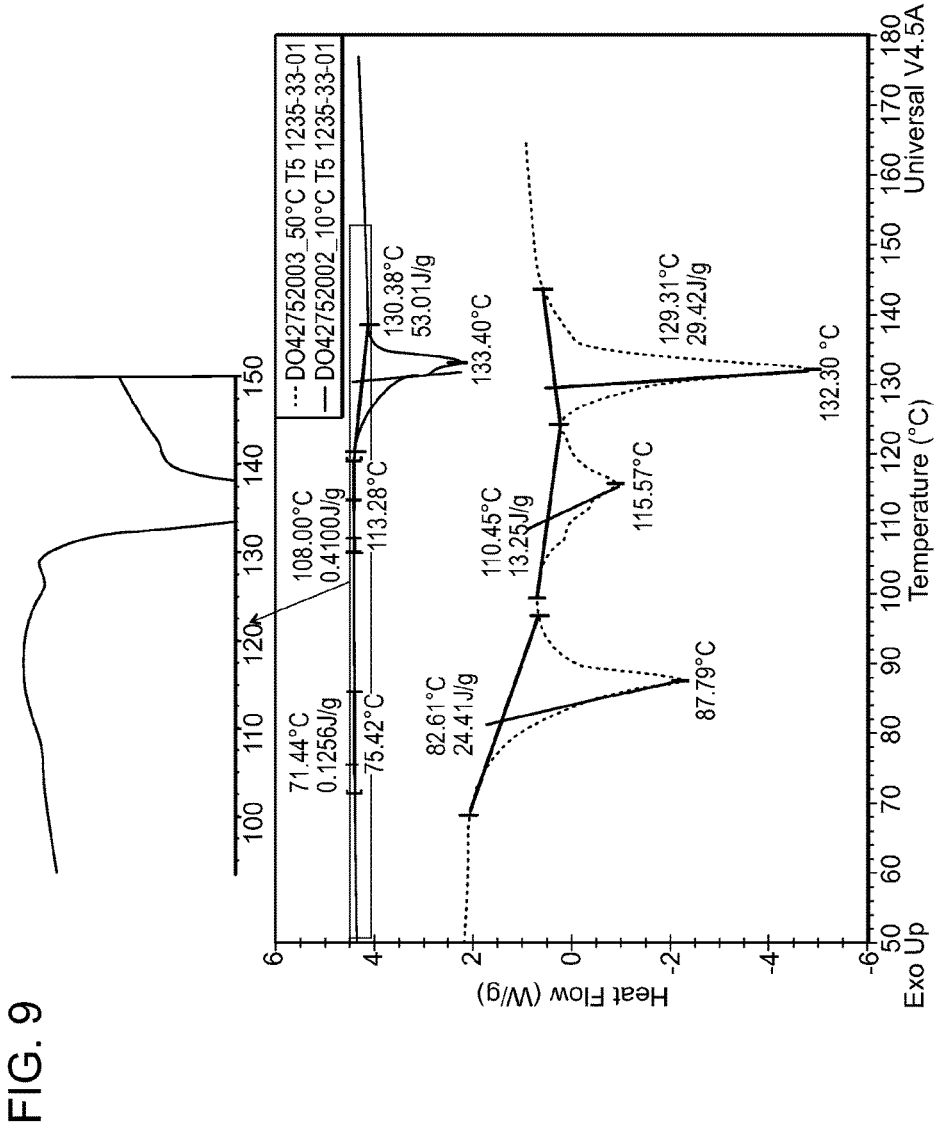
FIG. 9: depicts DSC thermograms of an anhydrous form of compound 5 (Form 2). The top thermogram was obtained by heating at a rate of 10° C./min, and the bottom thermogram was obtained by heating at a rate of 50° C./min.
Figure 10:
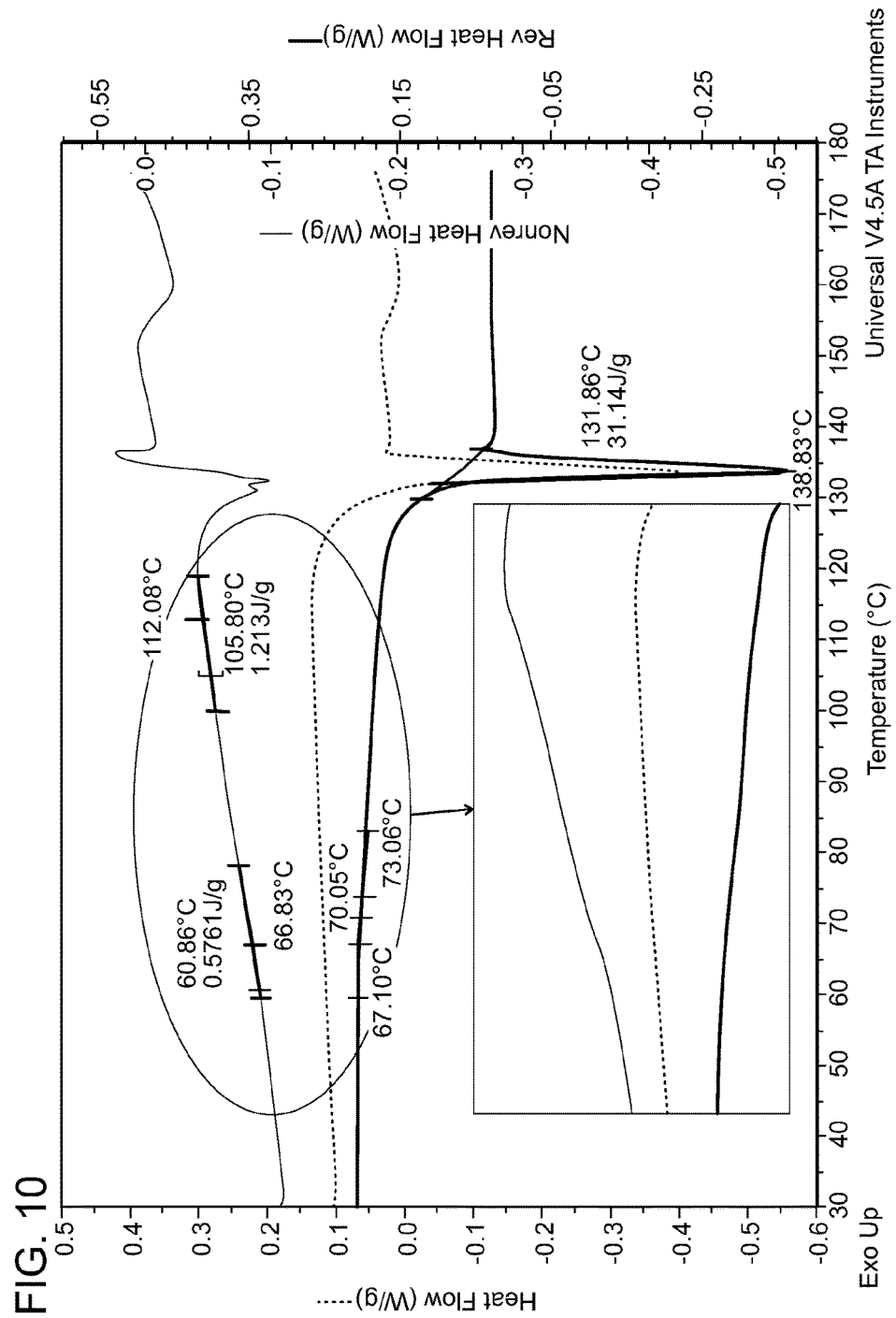
FIG. 10: depicts a modulated DSC thermogram of an anhydrous form of compound 5 (Form 2).

Form 2 transformed to Form 1 upon heating as confirmed by VT-XRPD and DSC. The DSC thermograms (FIG. 9) for the sample showed three main events at the heating rates employed (10 and 50° C./min). A modulated DSC experiment was performed to determine the thermodynamic or kinetic nature of these events from the reversible and non-reversible heat flow thermograms respectively (FIG. 10). The first event in the range 65-85° C. may be a glass transition as a step change is present in the reversible heat flow thermogram. The second event in the range 100-125° C. is present in the non-reversible heat flow trace and is attributable to the polymorphic transformation from Form 2 to Form 1 as seen by VT-XRPD. The third event in the range from 125-140° C. has both reversible and non-reversible components. The reversible component may be attributable to the melt of Form 1. Table 3 captures the characterization data for Compounds 14 and 5.

TABLE 3

Characterization Data for Anhydrous Crystalline Forms of Compounds 5 and 14

| Technique | | Compound 14 | Compound 5 (Anhydrous Form 1) | Compound 5 (Anhydrous Form 2) |
|---|---|---|---|---|
| XRPD | | Crystalline (Form 1) | Crystalline (Form 1/Pattern 1) | Crystalline (Form 2/Pattern 2) |
| VT-XRPD | | Not performed | Not performed | Conversion to Form 1 starts at 105° C. |
| XRPD stability post 7 days at | 40° C. & 75% RH | Unchanged by XRPD | Unchanged by XRPD | Unchanged by XRPD |
| | 25° C. & 96% RH | Unchanged by XRPD | Unchanged by XRPD | Unchanged by XRPD |
| $^1$H NMR | | Consistent with structure of 14 (1.0 eq. of p-toluenesulfonic acid; trace amount of crystallising solvents) | Consistent with structure of 5 (trace amount of crystallising solvents) | Consistent with structure of 5 (0.005 eq IPA present) |
| Thermal | DSC @ 10° C./min | Endothermic event with onset at 155.4° C. (71.9 J/g); broad endothermic event at 232.2° C. (205.0 J/g) | Endotherm at 129.0° C. (−46 J/g), Decomposition exotherm at ~200° C. | Shallow endotherms in the range 65-85° C. & 100-120° C., Multiple endotherms at 125-140° C. (−53 J/g) |
| | DSC @ 50° C./min | Not performed | Not performed | Broad endotherms in the range 65-95° C. & 110-125° C., Endotherm 129.3° C. (−29 J/g) |
| | mDSC | Not performed | Not performed | Reversible = step change 60-80° C., Endotherm at 131.9° C. (−31.14 J/g); Non-reversible = Endotherm 60-80° C., Exotherm at 105-120° C. |
| | TGA | 0.25% (30-150° C.); 4.3% (150-250° C.) Decomposition onset at ~300° C. | 0.1% (50-150° C.) Decomposition onset at ~200° C. | 0.2% (50-150° C.) Decomposition onset at ~200° C. |
| HPLC | | 99.2% by area | 97.2% by area | 97.9% by area |
| GVS | | ca. 1.6% water uptake over 0-90% RH range; (no hysteresis observed) | ca. 1.3% water uptake over 0-90% RH range (slight hysteresis observed) | ca. 0.7% water uptake over 0-90% RH range (no hysteresis observed) |
| XRPD post GVS | | unchanged | unchanged | unchanged |
| SEM | | | Agglomerates up to 200 µm in size | Agglomerates up to 200 µm in size |
| FT-IR | | | Spectral Pattern Characteristic bands/cm$^{-1}$: 3363, 3151, 2234, 2218, 1607, 1512, 1504, 1251, 1097, 972, 831, 818 | Spectral Pattern Characteristic bands/cm$^{-1}$: 3393, 3150, 2230, 1608, 1512, 1504, 1252, 1096, 972, 832, 820 |

Example 12

Thermodynamic Stability Relationships of Form 1 and Form 2

The melt of Form 1 of compound 5 was determined by DSC to be at 129.0° C. with an enthalpy of −46 J/g. A melt endotherm was not determined for Form 2 as it transforms to Form 1 upon heating at different rates. Competitive slurry experiments were carried out to identify the most stable form at 5° C., 25° C. and 50° C. These experiments were performed in IPA, ethanol and toluene. To conduct these experiments a solid mixture of Forms 1 and 2 (<18 mg per sample) was suspended in the corresponding saturated solution of compound 5 and stirred at the desired temperature. Saturated solutions of compound 5 were prepared at 50° C. by dissolving 40 mg, 60 mg and 200 mg of sample in 1.4 mL of IPA, 0.8 mL of ethanol and 0.8 mL of toluene, respectively. The slurries were filtered, air-dried and analyzed by XRPD after stirring for up to 10 days at the desired temperature. Table 4 shows the results for the competitive slurry experiments. All the experiments except for that performed in IPA at 5° C. gave pure Form 1. The experiment in IPA at 5° C. remained a mixture of Form 1 and 2 after 10 days stirring. Form 1 is therefore the thermodynamically stable form of the pair Form 1/Form 2 in the temperature range investigated.

TABLE 4

Competitive slurry experiments of Compound 5 Form 1 and Form 2

| Experiment | Solid Mixture weight Form 1 | Form 2 | Volume of sat. solution added | Temp. | XRPD |
|---|---|---|---|---|---|
| 1 | 16.3 mg | 14.8 mg IPA | 400 μL | 50° C. | Form 1 |
| 2 | 16.6 mg | 16.8 mg Ethanol | 250 μL | 50° C. | Form 1 |
| 3 | 17.9 mg | 14.4 mg Toluene | 250 μL | 50° C. | Form 1 |
| 4 | 13.9 mg | 14.1 mg IPA | 400 μL | 25° C. | Form 1 |
| 5 | 15.6 mg | 14.7 mg Ethanol | 250 μL | 25° C. | Form 1 |
| 6 | 17.4 mg | 18.0 mg Toluene | 250 μL | 25° C. | Form 1 |
| 7 | 13.7 mg | 15.8 mg IPA | 400 μL | 5° C. | Form 1 |
| 8 | 13.1 mg | 17.3 mg Ethanol | 250 μL | 5° C. | Form 1 |
| 9 | 17.0 mg | 13.6 mg Toluene | 250 μL | 5° C. | Form 1 |

Further characterization of the various polymorph forms of compounds 5 and 14 are detailed in the accompanying figures.

Incorporation by Reference

The contents of all references (including literature references, issued patents, published patent applications, and co-pending patent applications) cited throughout this application are hereby expressly incorporated herein in their entireties by reference.

Equivalents

Those skilled in the art will recognize, or be able to ascertain using no more than routine experimentation, many equivalents of the specific embodiments of the invention described herein. Such equivalents are intended with be encompassed by the following claims.

What is claimed:

1. A polymorph of a compound of formula 5,

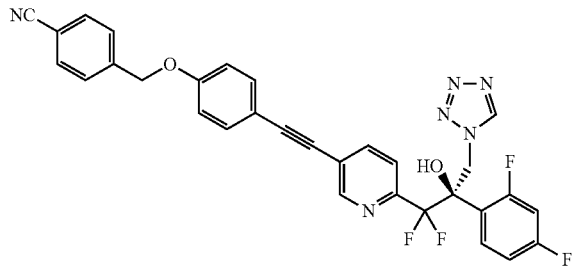

characterized by at least one of:
(i) a powdered X-ray diffraction pattern having two or more peaks expressed in degrees 2-theta±0.2° and selected from peaks delineated in the pattern of FIG. 8; or
(ii) a DSC thermogram showing an endotherm at about 65-85° C.

2. The polymorph of claim 1, characterized by a powdered X-ray diffraction pattern having peaks expressed in degrees 2-theta±0.2° at each of about 10.9, 14.0, 15.9, 19.7, and 23.2.

3. The polymorph of claim 1, wherein the polymorph has less than 1.0% water therein.

* * * * *